US007608281B2

(12) United States Patent
Underhill et al.

(10) Patent No.: US 7,608,281 B2
(45) Date of Patent: Oct. 27, 2009

(54) COMPOSITION AND USE OF RAR ANTAGONISTS FOR PROMOTING CHONDROGENESIS

(75) Inventors: Tully Michael Underhill, London (CA); Andrea Dawn Weston, London (CA)

(73) Assignee: T. Michael Underhill, Vancouver, British Columbia (CA)

( * ) Notice: Subject to any disclaimer, the term of this patent is extended or adjusted under 35 U.S.C. 154(b) by 85 days.

(21) Appl. No.: 11/652,820

(22) Filed: Jan. 12, 2007

(65) Prior Publication Data

US 2007/0134198 A1    Jun. 14, 2007

Related U.S. Application Data

(63) Continuation of application No. 09/856,324, filed as application No. PCT/CA99/01106 on Nov. 19, 1999, now Pat. No. 7,186,418.

(51) Int. Cl.
*A61F 2/28* (2006.01)
(52) U.S. Cl. ........................................ 424/426
(58) Field of Classification Search ............... None
See application file for complete search history.

(56) References Cited

U.S. PATENT DOCUMENTS

| 4,235,871 A | 11/1980 | Papahadjopoulos et al. |
| 4,762,915 A | 8/1988 | Kung et al. |
| 5,827,500 A | 10/1998 | Demarchez et al. |
| 5,877,207 A | 3/1999 | Klein et al. |
| 6,184,256 B1 | 2/2001 | Basset et al. |
| 6,326,397 B1 | 12/2001 | Bollag et al. |

FOREIGN PATENT DOCUMENTS

| JP | 10-114757 | | 5/1998 |
| WO | WO 98/08546 | * | 3/1998 |
| WO | WO 99/24415 | | 5/1999 |
| WO | WO 99/33821 | | 7/1999 |

OTHER PUBLICATIONS

Bramlage et al, "Decrease in Expression of Bone Morphogenic Proteins in Synovial Tissue of Pateients with Osteoarthritis and Rheumatoid Arthritis", Arthritis Research & Therapy, 8(3):R58 2006.*

Adams, Mark E., et al., The role of viscosupplementation of hylan G-F 20 (*Synvisc®*) in the treatment of osteoarthritis of the knee: a Canadian multicenter trial comparing hylan G-F 20 alone, hylan G-F 20 with non-steroidal anti-inflammatory drugs (*NSAIDs*) and NSAIDs alone, *Osteoarthirtis and Cartilage*, vol. 213, pp. 213-226 (1995).

Ahrens, Marion, et al., Expression of Human Bone Morphogenetic Proteins-2 or-4 in Murine Mesenchymal Progenitor C3H10T½ Cells Induces Differentiation in to Distinct Mesenchymal Cell Lineages, *DNA and Cell Biology*, vol. 12, No. 10, pp. 871-880 (1993).

(Continued)

*Primary Examiner*—Carlos A. Azpuru
(74) *Attorney, Agent, or Firm*—Finnegan, Henderson, Farabow, Garrett & Dunner LLP

(57) ABSTRACT

The invention provides compositions comprising a RAR antagonist for promoting chondrogenesis and to methods employing such compositions for treating cartilage and associated bone abnormalities resulting from injury or disease and for ex vivo tissue engineering.

15 Claims, 9 Drawing Sheets

OTHER PUBLICATIONS

Amos, Brad, et al., Retinoid-Sensitive Cells and Cell Lines, *Methods in Enzymology*, vol. 190, pp. 217-225 (1990).

Apfel, C., et al., A retinoic acid receptor α antagonist selectively counteracts retinoic acid effects, *Proc. Natl. Acad. Sci. USA*, vol. 89, pp. 7129-7133 (Aug. 1992).

Brunet, Lisa J., et al., Noggin, Cartilage Morphogenesis, and Joint Formation in Mammalian Skeleton, *Science*, vol. 280, pp. 1455-1457 (May 29, 1998).

Capdevila, Javier, et al., Endogenous and Ectopic Expression of noggin Suggests a Conserved Mechanism for Regulationof BMP Function during limb and Somite Patterning, *Developmental Biology*, vol. 197, pp. 205-217 (1998).

Cash, David E., et al., Retinoic Acid Receptor α Function in Vertebrate Limb Skeletogenesis: a Modulator of Chondrogenesis, *The Journal of Cell Biology*, vol. 136, pp. 445-457 (Jan. 27, 1997).

Chambon, Pierre, A decade of molecular biology of retinoic acid receptors, *FASEB J.*, vol. 10, pp. 940-954 (1996).

Doilé, Pascal, et al., Differential expression of genes encoding α, β and γ retinoic acid receptors and CRABP in the developing limbs of the mouse, *Nature*, vol. 342, pp. 702-705 (Dec. 7, 1989).

Duke, Jackie, et al., Effect of the Brachypod Mutation on Early Stages of Chondrogenesis in Mouse Embryonic Hind Limbs: An Ultrastructural Analysis, *Teratology*, vol. 19, pp. 367-376 (1979).

Duprez, D.M., et al, Bone Morphogenetic Protein-2 (*BMP-2*) Inhibits Muscle Development and Promotes Cartilage Formation in Chick Limb Bud Cultures, *Developmental Biology*, vol. 174, pp. 448-452 (1996).

Duprez, Delphine, et al., Overexpression of BMP-2 and BMP-4 alters the size and shape of developing skeletal elements in the chick limb, *Mechanisms of Development*, vol. 57, pp. 145-157 (1996).

Eckhardt, Karl, et al., A retinoic acid receptor α antagonist counteracts retinoid teratogenecity in vitro and reduced incidence and/or severity of malformations in vivo, *Toxicology Letters*, vol. 70, pp. 299-308 (1994).

Eyrolles, Laurence, et al., Retinobenzoic Acids. 6. Retinoid Antagonists with a Heterocyclic Ring, *J. Med. Chem.*, vol. 37, pp. 1508-1517 (1994).

Ghyselinck, Norbert B., et al., Role of the retinoic acid receptor beta (*RARβ*) during mouse development, *Int. J. Dev. Biol.*, vol. 41, pp. 425-447 (1997).

Giguere, Vincent, et al., Identification of a receptor for the morphogen retinoic acid, *Nature*, vol. 330, pp. 624-629 (Dec. 17, 1987).

Hall, B.K., et al., The membranous skeleton: the role of cell condensations in vertebrate skeletogenesis, *Anatomy and Embryology*, vol. 186, pp. 107-124 (1992).

Hall, Brian K., et al., Divide, accumulate, differentiate: cell condensation in skeletal development revisited, *Int. J. Dev. Biol.*, vol. 39, pp. 881-893 (1995).

Hogan, Brigid L.M., Bone morphogenetic proteins in development, *Current Opinion in Genetics and Development*, vol. 6, pp. 432-438 (1996).

Ide, H., et al., Retinoic Acid Promotes Proliferation and Chondrogenesis in the Distal Mesodermal Cells of Chick Limb Bud, *Development Biology*, vol. 130, pp. 767-773 (1988).

International Search Report, International Application No. PCT/CA99/01106.

Jiang, Heng, et al., Modulation of limb bud chondrogenesis by retinoic acid and retinoic acid receptors, *Int. J. Dev. Biol.*, vol. 39, pp. 617-627 (1995).

Jones, C. Michael, et al., Involvement of Bone Morphogenetic Protein-4 (*BMP-4*) and Vgr-1 in morphogenesis and neurogenesis in the mouse, *Development*, vol. 111, pp. 531-542 (1991).

Kastner, Philippe, et al., Vitamin A deficiency and mutations of RXRα, RXRβ amd RARα lead to early differentiation of embryonic ventricular cardiomyocytes, *Development*, vol. 124, pp. 4749-4758 (1997).

Keneko, Satoru, et al., Retinoid Antagonists, *Med. Chem. Res.*, vol. 1, pp. 220-225 (1991).

Kingsley, David M., et al., The Mouse short ear Skeletal Morphogenesis Locus is Associated with Defects in a Bone Morphogenetic Member of the TGFβ Superfamily, *Cell*, vol. 71, pp. 399-410 (Oct. 30, 1992).

Kingsley, David M., The TGF-β superfamily: new members, new receptors, and new genetic tests of function in different organisms, *Genes & Development*, vol. 8, pp. 133-146 (1994).

Kistler, Andreas, Limb bud cell cultures for estimating the teratogenic potential of compounds; Validation of the test system with retinoids, *Archives of Toxicology*, vol. 60, pp. 403-414 (1987).

Kochhar, D.M., Limb Development in Mouse Embryos, *Teratology*, vol. 7, pp. 289-298 (1973).

Kochhar, Devendra M., et al., The use of a retinoid receptor antagonist in a new model to study vitamin A-dependent development events, *Int. J. Dev. Biol.*, vol. 42, pp. 601-608 (1998).

Koyama, E., et al., Retinoids and Their Nuclear Receptors Promote the Completion of Chrondrocyte Maturation During Limb Skeletogenesis, Abstract, *Chondrogenesis and Osteogenesis*, p. 71a.

Koyama, Eiki, et al., Retinoid Signaling is Required for Chrondrocyte Maturation and Endochondral Bone Formation during Limb Skeletogenesis, *Developmental Biology*, vol. 208, pp. 375-391 (1999).

Kwasigroch, T.E., et al., Production of Congenital Limb Defects with Retinoic Acid: Phenomenological Evidence of Progressive Differentiation During Limb Morphogenesis, *Anat. Embryol.*, vol. 161, pp. 105-113 (1980).

Lee, Kenneth K.H., et al., Influence of Digits, Ectoderm, and Retinoic Acid on Chondrogenesis by Mouse Interdigital Mesoderm in Culture, *Developmental Dynamics*, vol. 201, pp. 297-309 (1994).

Lohnes, David, et al., Function of Retinoic Acid Receptor γ in the Mouse, *Cell*, vol. 73, pp. 643-658 (May 21, 1993).

Lohnes, David, et al., Function of the retinoic acid receptors (*RARs*) during development (*I*) Craniofacial and skeletal abnormalities in RAR double mutants, *Development*, vol. 120, pp. 2723-2748 (1994).

Lufkin, Thomas, et al., High postnatal lethality and testis degeneration in retinoic acid receptor α mutant mice, *Proc. Natl. Acad. Sci. USA*, vol. 90, pp. 7225-7229 (Aug. 1993).

Luo, Guangbin, et al., BMP-7 is an inducer of nephrogenesis, and is also required for eye development and skeletal patterning, *Genes & Development*, vol. 9, pp. 2808-2820 (1995).

Luo, Jiangming, et al., Mice lacking all isoforms of retinoic acid receptor β develop normally and are susceptible to the teratogenic effects of retinoic acid, *Mechanisms of Development*, vol. 53, pp. 61-71 (1995).

Lussier, Marc, et al., Interdigital soft tissue separation induced by retinoic acid in mouse limbs cultured in vitro, *Int. J. Dev. Biol.*, vol. 37, pp. 555-564 (1993).

Lyons, Karen M., et al., Organogenesis and pattern formation in the mouse: RNA distribution patterns suggest a role for Bone Morphogenetic Protein-2A (*BMP-2A*), *Development*, vol. 109, pp. 833-844 (1980).

Macias, D., et al., Role of BMP-2 and OP-1 (*BMP-7*) in programmed cell death and skeletogenesis during chick limb development, *Development*, vol. 124, pp. 1109-1117 (1997).

Mangelsdorf, David J., et al., The Retinoid Receptors, *The Retinoids: Biology, Chemistry, and Medicine*, vol. 319-349 (1994).

Marigo, Valeria, et al., Sonic hedgehog Differentially Regulates Expression of FLI and GLI3 during Limb Development, *Developmental Biology*, vol. 180, pp. 273-283 (1996).

McBurney, M.W., et al., Control of muscle and neuronal differentiation in a cultured embryonal carcinoma cell line, *Nature*, vol. 299, pp. 165-167 (Sep. 9, 1982).

Mendelsohn, C., et al., Developmental analysis of the retinoic acid-inducible RAR-β2 promoter in transgenic animals, *Development*, vol. 113, pp. 723-734 (1991).

Minas, Tom, et al., Current Concepts in the Treatment of Articular Cartilage Defects, *Orthopedics*, vol. 20, pp. 525-538 (1997).

Moses, Harold L., et al., Regulation of differentiation by TGF-β, *Current Opinion in Genetics and Development*, vol. 6, No. 5, pp. 581-586 (1996).

Nuka, Satoshi, et al., All-trans Retinoic Acid Inhibits Dexamethasone-induced ALP Activity and Mineralization in Human Osteoblastic Cell Line SV HFO, *Cell Structure and Function*, vol. 22, pp. 27-32 (1997).

Paulsen, Douglas F., et al., Stable, Position-Related Responses to Retinoic Acid by Chick Limb-Bud Mesenchymal Cells in Serum-Free Cultures, In Vitro *Cell. Dev. Biol.*, vol. 30A, pp. 181-186 (Mar. 1994).

Paulsen, Douglas F., et al., Stage- and Region-Dependent Responses of Chick Wing-Bud Mesenchymal Cells to Retinoic Acid in Serum-Free Microcultures, *Developmental Dynamics*, vol. 201, pp. 310-323 (1994).

Roark, Eileen F., et al., Transforming Growth Factor-β and Bone Morphogenetic Protein-2 Act by Distinct Mechanisms to Promote Chick Limb Cartilage Differentiation in Vitro, *Developmental Dynamics*, vol. 200, pp. 103-116 (1994).

Rosen, Vicki, et al., Purification and Molecular Cloning of a Novel Group of BMPs and Locationization of BMP mRNA in Developing Bone, *Connective Tissue Research*, vol. 20, pp. 313-319 (1989).

Rosen, Vicki, et al., Signaling Pathways in Skeletal Formation: A Role for BMP Receptors, *Annals New York Academy of Sciences*, vol. 785, pp. 59-69 (1996).

Ruberte, Esther, et al., Specific spatial and temporal distribution of retinoic acid receptor gamma transcripts during mouse embryogenesis, *Development*, vol. 108, pp. 213-222 (1990).

Sandell, Linda J., et al., Alternative Splice Form of Type II Procollagen RNA (*IIA*) is Predominant in Skeletal Precursors and Non-Cartilaginous Tissues During Early Mouse Development, *Developmental Dynamics*, vol. 199, pp. 129-140 (1994).

Sandell, Linda J., et al., Alternatively Spliced Type II Procollagen mRNAs Define Distinct Populations of Cells during Vertebral Development: Differential Expression of the Amino-Propeptide, *The Journal of Cell Biology*, vol. 114, No. 6, pp. 1307-1319.

Shenefelt, Ray E., Morphogenesis of Malformations in Hamsters Caused by Retinoic Acid: Relation to Dose and Stage at Treatment, *Teratology*, vol. 5, pp. 103-118 (1972).

Solloway, Mark, J., et al., Mice Lacking Bmp6 Function, *Developmental Genetics*, vol. 22, pp. 321-339 (1998).

Standeven, Andrew M.. et al., Retinoid-Induced Epiphyseal Plate Closure in Guinea Pigs, *Fundamental and Applied Toxicology*, vol. 34, pp. 91-98 (1996).

Storm, Elaine E., et al., Limb alterations in brachypodism mice due to mutations in a new member of the TGFβ-superfamily, *Nature*, vol. 368, pp. 639-643 (Apr. 14, 1994).

Teng, M., et al., Identification of highly potent retinoic acid receptor α-selective antagonists. *J. Med. Chem*, vol. 40, pp. 2445-2451 (1997).

Underhill, .T. Michael, et al., Constitutively Active Retinoid Receptors Exhibit Interfamily and Intrafamily Promoter Specificity, *Molecular Endocrinology*, vol. 8, No. 3, pp. 274-285 (1994).

Underhill, T. Michael, et al., Retinoids and Their Receptors in Skeletal Development, *Microscopy Research and Technique*, vol. 43, pp. 137-155 (1998).

Von Schroeder, Herbert P., The Effects of Natural and Synthetic Retinoids on the Differentiation of RCJ C5.18 Chondrogenic Cells, *Teratology*, vol. 50, pp. 54-62 (1994).

Wang, E. A., et al., Bone Morphogenetic Protein-2 Causes Commitment and Differentiation in C3H10T1/2 and 3T3 Cells, *Growth Factors*, vol. 9, pp. 57-71 (1993).

Winnier, Glenn, et al., Bone morphogenetic protein-4 is required for mesoderm formation and patterning in the mouse, *Genes & Development*, vol. 9, pp. 2105-2116 (1995).

Wolpert, Lewis, Signals in limb development: Stop, Go, Stay and Position, *J. Cell Sci. Suppl.*, vol. 13, pp. 199-208 (1990).

Wozney, John M., et al., Bone Morphogenetic Protein and Bone Morphogenetic Protein Gene Family in Bone Formation and Repair, *Clinical Orthopaedics and Related Research*, vol. 346, pp. 26-37 (1998).

Yokouchi, Yuji, et al., BMP-2/03 mediate programmed cell death in chicken limb buds, *Development*, vol. 122, pp. 3725-3734 (1996).

Yoshimura, Hiroyuki, et al., A Novel Type of Retinoic Acid Receptor Antagonist: Synthesis and Structure-Activity Relationships of Heterocyclic Ring-Containing Benzoic Acid Derivatives, *J. Med. Chem.*, vol. 38, pp. 3163-3173 (1995).

Zhang, Hongbing, et al., Mice deficient for BMP2 are nonviable and have defects in amnion/chorion and cardiac development, *Development*, vol. 122, pp. 2977-2986 (1996).

Zou, Hongyan, et al., Distinct roles of type I bone morphogenetic protein receptors in the formation and differentiation of cartilage, *Genes & Development*, vol. 11, pp. 2191-2203 (1997).

Zou, Hongyan, et al., Requirement for BMP Signaling in Interdigital Apoptosis and Scale Formation, *Science*, vol. 272, pp. 738-741 (May 3, 1996).

Koyama, E., et al., Retinoids and Their Nuclear Receptors Promote the Completion of Chondrocyte Maturation During Limb Skeletogenesis, Abstract, *Matrix Biology*, vol. 17, No. 2, p. 155 (Jun. 1998).

* cited by examiner

COMPOSITION AND USE OF RAR ANTAGONISTS FOR PROMOTING CHONDROGENESIS

STATEMENT OF PRIORITY

The present invention is a continuation of U.S. application Ser. No. 09/856,324 (allowed), having a filing date of Aug. 23, 2001 now U.S. Pat. No. 7,186,418, which is a 35 U.S.C. § 371 national phase application of PCT Application No. PCT/CA99/01106, having an international filing date of Nov. 19, 1999, and which claims priority to Canadian Application No. 2,254,429, filed Nov. 19, 1998, the entire contents of each of which are incorporated by reference herein.

FIELD OF THE INVENTION

The invention relates to compositions for promoting chondrogenesis and to methods for treating cartilage and bone abnormalities resulting from injury or disease and for ex vivo tissue engineering.

BACKGROUND OF THE INVENTION

Retinoic acid (RA) is known to have an important signalling role in the regulation of embryonic development and cell differentiation. The biological effects of RA are transduced via two classes of nuclear receptors, designated retinoic acid receptors (RARα, RARβ and RARγ) and retinoid X receptors (RXRα, RXRβ and RXRγ) (Giguere et al., (1987), Nature, 350, 624-629).

Many studies have been made of the role of RA and its receptors in the process of chondrogenesis and skeletal development. For example, down regulation of RARα has been stated to be important for chondrogenic expression (Cash et al. (1997) J. Cell Biol. 136, 445-457). Down regulation of RAR-β2 using antisense oligonucleotides was found to stimulate chondrogenesis and thus it was suggested that RAR-β2 helps to prevent mesenchymal cells from expressing their chondrogenic bias. Underhill et al. (1998) Micro. Res. Tech. 43, 137-155 reported that abnormal expression of RARs inhibits chondrogenesis. However, it was also found that absence of RAR can lead to deficiencies in cartilage formation while also promoting chondrogenesis at ectopic sites.

Addition of RA and RAR-specific agonists has been shown to inhibit cartilage formation in limb bud micromass cultures, and act as a teratogen in vivo to negatively affect skeletal development (Kistler (1987) Arch. Toxicol. 60, 403-414; Kochhar (1973) Teratology 7, 289-295; Kochhar and Aydelotte (1974) J. Embryol. Exp. Morph. 31, 721-734; Kwasigrich and Kochhar (1980) Anat. Embryol. 161, 105-113. In contrast, addition of retinoic acid to micromass cultures has also been demonstrated to stimulate cartilage formation (Paulsen et al. (1994) Dev. Dynam. 201, 310-323; Paulsen et al. (1994) Dev. Biol. 30A, 181-186).

Addition of an RAR antagonist completely reversed the inhibitory action of an RAR agonist on chondrocyte differentiation in rat and mouse embryo limb bud mesenchymal cells in vitro (Eckhardt and Schmitt (1994) Toxicol. Letters, 70, 299-308; Kocchar et al. (1998) Int. J. Dev. Biol., 42, 601-608). These authors, however, found that the antagonist alone had no effect on limb bud mesenchymal cell differentiation.

The precise role of RARs in chondrogenesis was unclear from these studies. Specifically, it was unclear whether RARs functioned to inhibit chondrogenesis or stimulate that process. Overall, the role of RAR antagonists in the process of chondrogenesis was not clearly established.

SUMMARY OF THE INVENTION

It has now been demonstrated that RAR activity alone has a fundamental role in controlling the transition of chondro-progenitor cells into chondrocytes. It has also now been demonstrated that administration of RAR antagonists can initiate chondrogenesis and stimulate cartilage formation in vitro and in vivo. Furthermore, it is now also demonstrated that administration of a RAR antagonist can rescue cartilage formation. This provides a basis for the development of therapeutic compositions and uses of such compositions to treat disorders involving abnormal cartilage formation.

The present invention now provides therapeutic compositions and methods for the treatment of disorders involving abnormal cartilage formation and associated abnormal skeletal development resulting from disease or due to trauma.

In accordance with one embodiment, the present invention provides a pharmaceutical composition comprising an effective amount of an RAR antagonist and, optionally, a pharmaceutically acceptable carrier.

RAR antagonists for use in the present invention are characterized by having a stimulating effect on cartilage formation and as a result on associated bone development in a vertebrate. RAR antagonists may be defined as any chemical that binds to one or more of the RAR subtypes with a Kd of less than 1 micromolar. Conventionally, a RAR antagonist is a chemical agent that inhibits the activity of an RAR agonist.

In accordance with a further embodiment, the invention provides a method for stimulating cartilage formation in a vertebrate, the method comprising administering to the vertebrate an effective cartilage formation stimulating amount of an RAR antagonist.

In accordance with a further embodiment, the invention provides a method for treating damaged cartilage and associated bone in a subject, comprising administering to the subject an effective amount of an RAR antagonist, wherein the RAR antagonist stimulates cartilage repair and formation which mediates associated bone repair.

In accordance with a further embodiment, the invention provides a method for enhancing osseous integration of orthopedic or dental implants in a subject comprising administering to the subject an effective amount of an RAR antagonist.

In accordance with a further embodiment, the invention provides a method for treating arthritis in a subject, comprising administering to the subject an effective amount of an RAR antagonist.

In accordance with a further embodiment, the invention provides a method for treating arthritis in a subject, comprising administering to the subject chondrogenic cells treated with an effective amount of an RAR antagonist.

According to one embodiment of the invention, there is provided a composition for inducing chondrogenesis and associated skeletal development in a vertebrate, the composition comprising:
  a RAR antagonist; and
  a pharmaceutically acceptable carrier.

According to another embodiment of the invention, there is provided a morphogenic device for implantation at a cartilage site in a vertebrate, the device comprising:
  an implantable biocompatible carrier; and
  a RAR antagonist dispersed within or on said carrier.

According to yet another embodiment of the invention, there is provided the use of a composition comprising a RAR antagonist and a pharmaceutically acceptable carrier, for inducing chondrogenesis in vitro.

According to yet another embodiment of the invention, there is provided a method for producing a chondrocyte from a chondroprogenitor mesenchymal cell comprising contacting a chondroprogenitor mesenchymal cell with a RAR antagonist in vitro.

According to another embodiment of the invention, there is provided an implantable prosthetic device for repairing cartilage-associated orthopedic defects, injuries or anomalies in a vertebrate, the device comprising:
  a prosthetic implant having a surface region implantable adjacent to or within a cartilage tissue.
  a RAR antagonist composition disposed on the surface region in an amount sufficient to promote enhanced cartilage growth into the surface.

According to another embodiment of the invention, there is provided a method for promoting in vivo integration of an implantable prosthetic device into a target cartilage tissue of a vertebrate, the method comprising the steps of:
  providing on a surface of the prosthetic device a composition comprising a RAR antagonist and a pharmaceutically acceptable carrier and
  implanting the device in a vertebrate at a site where the target cartilage tissue and the surface of the prosthetic device are maintained at least partially in contact for a time sufficient to permit tissue growth between the target cartilage tissue and the device.

According to yet another embodiment of the invention, there is provided a method for promoting natural bone formation at a site of skeletal surgery in a vertebrate, the method comprising the steps of delivering a RAR antagonist composition to the site of the skeletal surgery whereby such delivery indirectly promotes the formation of new bone tissue mediated by cartilage.

According to another embodiment of the invention, there is provided a method for repairing large segmental skeletal gaps and non-union fractures arising from trauma or surgery in a vertebrate, the method comprising delivering a RAR antagonist composition to the site of the segmental skeletal gap or non-union fracture whereby such delivery promotes the formation of cartilage which mediates new bone tissue formation.

According to yet another embodiment of the invention, there is provided a method for aiding the attachment of an implantable prosthesis to a cartilage site and for maintaining the long term stability of the prosthesis in a vertebrate, the method comprising coating selected regions of an implantable prosthesis with a RAR antagonist composition and implanting the coated prosthesis into the cartilage site, whereby such implantation promotes the formation of new cartilage tissue and indirectly stimulates bone formation.

According to a further embodiment of the invention, there is provided a method of producing cartilage at a cartilage defect site in vivo, the method comprising:
  implanting into the defect site a population of chondrogenic cells which have been cultured in vitro in the presence of a RAR antagonist.

According to another embodiment of the invention, there is provided a method for treating a degenerative joint disease characterized by cartilage degeneration, the method comprising:
  delivering a therapeutically effective amount of a RAR antagonist to a disease site.

BRIEF DESCRIPTION OF THE DRAWINGS

The present invention will be further understood from the following description with reference to the Figures, in which.

DETAILED DESCRIPTION OF THE INVENTION

Figure 1:
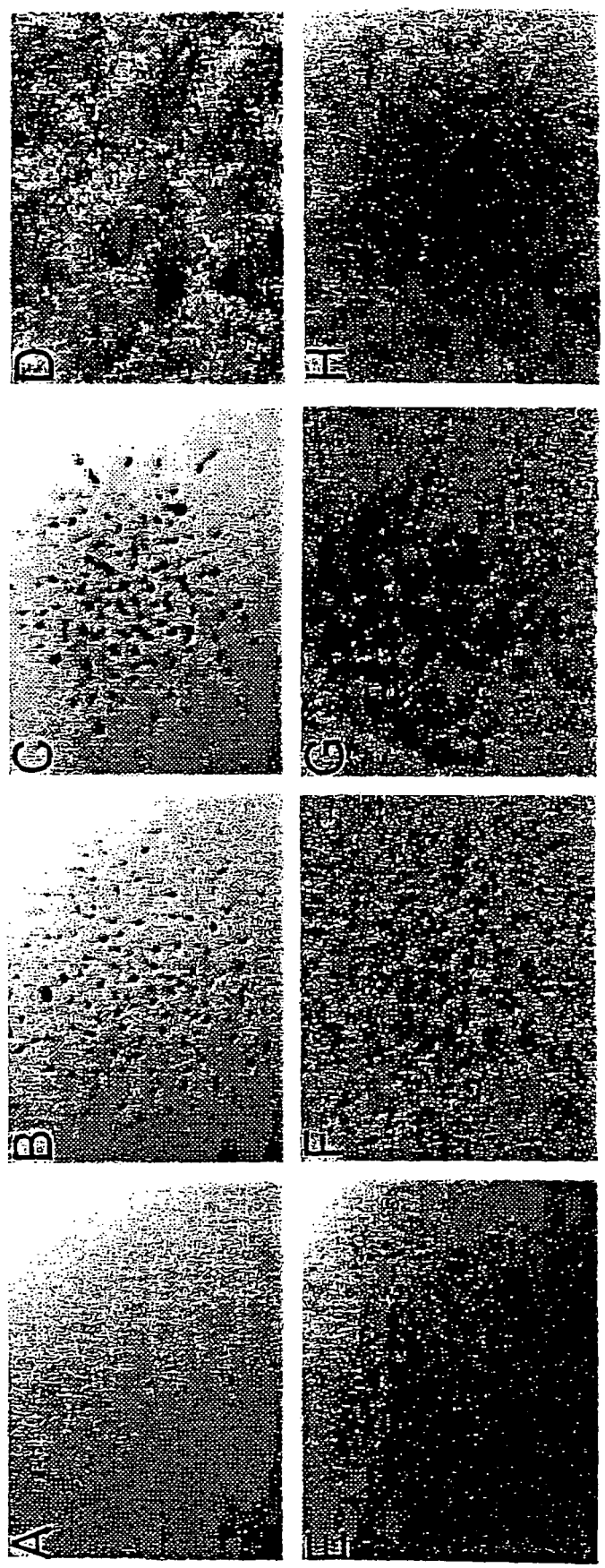
FIG. 1 shows photomicrographs of transgene-expressing cells. Panels (A-C) show wild-type fore limb cultures stained with alcian blue on days 2, 4 and 6. Panels (D-G) show transgenic fore limb cultures stained with magental-gal followed by alcian blue at days 2, 4 and 6. Panel (D) shows higher magnification of day 4 transgenic fore limb cultures. Transgene-expressing cells are excluded from the cartilage nodules. Panel (H) shows day 4 transgenic hind limb cultures. Transgene-expressing cells are much more abundant compared to fore limb cultures, and hence only a few small cartilage nodules have formed. Bar: (A-C, E-H) 1.0 mm (D) 0.4 mm.

The present inventors have demonstrated the use and effectiveness of RAR antagonists to stimulate chondrogenesis and skeletal development.

Limb Bud Development

Patterning of the vertebrate limb bud relies on the cooperative action of several signalling centres. Signals have been identified that emanate from the apical ectodermal ridge (AER), ventral ectoderm (VE) and a region within the distal posterior margin termed the zone of polarizing activity (ZPA). The AER is important in specifying proximodistal axial identity, while the VE and ZPA are important in determining dorsal/ventral and anteroposterior identity, respectively. Each is essential for the proper patterning and outgrowth of the limb, and their perturbation results in defects of the paraxial skeleton. The mechanism by which these patterning cues influence mesenchyme commitment is thought to occur within the progress zone (PZ) which underlies the AER. Cells within the progress zone receive signals from all three signaling centres, integrating them into a positional identity that is fixed as the cells leave the PZ during limb outgrowth. Shortly thereafter this positional identity is translated into a cell identity and the corresponding differentiation program is initiated. With respect to skeletal formation, these signals culminate in the commitment of mesenchymal cells to the chondrocytic lineage.

Bones within the limb are formed from a cartilage precursor and the cartilage forms from condensed mesoderm. These condensations represent the earliest stages of limb patterning and are considered to be the forbears of the mature limb bones (Ede (1983) Cellular condensations and chondrogenesis. in Cartilage: Development, Differentiation and Growth, B. K. Hall, ed. (New York: Academic Press), pp. 143-185. Following condensation, the mesodermal cells in the interior of each condensation differentiate into chondrocytes. This differentiation occurs in concert with limb outgrowth, such that proximal mesenchymal cells (close to the body wall) that are fated to become chondrocytes differentiate prior to more distal cells. The spatiotemporal regulation of mesenchyme differentiation into chondrocytes is a crucial step in endochondral bone formation in that it preserves the pattern of the bone primordia established earlier in limb development and provides a suitable matrix for subsequent ossification. Despite the importance of this stage in skeletal development, mechanisms that control mesenchyme differentiation into chondrocytes are poorly understood.

During limb outgrowth, signals that promote as well as inhibit chondrogenesis are important determinants in limb ontogeny (Wolpert, (1990) J. Cell Sci. Suppl. 13, 199-208. Many molecules have been identified that promote chondrogenesis in vivo and in vitro. Some of these include members of the transforming growth factor (TGF)-β superfamily, bone morphogenetic proteins (BMPs), gdf-5, and TGF-β-1, -2 and -3 (Hogan (1996) Curr. Opin. Genet. Dev. 6, 432-438; Kingsley (1994) Genes Dev. 8, 133-146; Moses and Serra (1996) Curr. Opin. Genet. Dev. 6, 581-586; Wozney and Rosen (1998) Clin. Ortho. Rel. Res. 346, 26-37. The importance of bmp-5 and gdf-5 in limb development is illustrated by the recent mapping of the classical mouse mutations for short ear and brachypod to their respective loci (Kingsley et al. (1992) Cell 71, 399-410; Storm et al. (1994) Nature 368, 639-643). Both of these mutants exhibit malformations in appendicular skeletal formation which, for the case of brachypod, has been attributed to a defect in chondrogenesis Duke and Elmer (1997) J. Embryol. Exp. Morph. 42, 209-217. Mice deficient in BMP-6 or BMP-7 also present with skeletal defects including delay in the ossification of the sternum in bmp-6−/− animals (Solloway et al. (1998) Dev. Genet. 22, 321-39) and polydactyly in the hind limbs of bmp-7−/− animals Luo et al. (1995) Genes Dev. 9, 2808-2820. Bmp-2 and -4 are expressed in condensing mesenchyme early in limb development then become localized to the interdigital mesenchyme and perichondrium (Jones et al. (1991) Development 111, 531-542; Lyons et al. (1990) Development 109, 833-844; Rosen et al. (1989) Connect Tissue Res 20, 313-319). Mouse embryos devoid of BMP-2 or BMP-4 do not survive beyond E9.5 (Winnier et al. (1995) Genes Dev. 9, 2105-2116; Zhang and Bradley (1996) Development 122, 2977-2986) making it difficult to elucidate their exact roles in skeletal development. It is known, however, that exogenously added BMP-2 or -4 under certain circumstances leads to overgrowth of the limb cartilages (Duprez et al. (1996) Mech. Dev. 57, 145-157; Duprez et al. (1996) Dev. Biol. 174, 448-452). Loss or gain-of-function of noggin, an inhibitor of BMP-2, -4 and -7, contributes to either overgrowth or a reduction in limb cartilages, respectively (Brunet et al. (1998) Science 280, 1455-1457; Capdevila and Johnson (1998) Dev Biol 197, 205-217). Together, these observations suggest an important role for the BMPs, especially BMPs -2 and -4 in formation of the cartilaginous elements of the limb bud.

It is well established that retinoic acid (RA), the active derivative of vitamin A is essential for normal embryonic development. Exposure of embryos to excess RA results in a range of defects depending not only on the dose of RA, but also on the timing of its administration (Shenfelt (1972) Teratology 5, 103-118). For instance when administered to E 11.5 to E 14.5 mouse embryos, large doses of RA cause limb defects (Kochar (1973) Teratology 7, 289-295; Kwasigroch and Kochar (1980) Anat. Embryol. 161, 105-113). This period during which RA treatment has the most dramatic effects on limb formation coincides with the timing of chondrogenesis in the limb bud.

RA exerts most of its biological effects primarily through receptors belonging to the steroid hormone family of nuclear receptors. There are two subfamilies of nuclear retinoid receptors, the RA receptors (RARs) and the retinoid X receptors (RXRs), with three subtypes of each ($\alpha$, $\beta$, and $\lambda$) (Chambon (1996) FASEB J. 10, 940-954; Mangelsdorf et al. (1994) "The retinoid receptors," in The Retinoids: Biology, Chemistry, and Medicine, Sporn, Roberts and Goodman, eds. (New York: Raven Press Ltd.), pp. 319-349. All three subtypes of the RARs have been suggested to have some role in chondrogenesis (Underhill and Weston, (1998) Micro. Res. Tech. 43, 137-155). The expression patterns of the RARs in the developing limb are consistent with their proposed roles in skeletal formation. Between E9.5 and E11.5, RAR$\alpha$ and $\lambda$ are expressed throughout the limb mesenchyme (Dolle et al. (1989) Nature 342, 702-705; Ruberte et al. (1990) Development 108, 213-222. Beyond this stage, RAR$\alpha$ is downregulated within the cartilaginous areas, while RAR$\lambda$ expression remains localized to these areas. RAR$\alpha$ expression becomes restricted to the interdigital region (IDR) overlapping with RAR$\beta$ expression at this time, and is also present in the perichondrium. In addition to being present in the IDR, RAR$\beta$ is expressed in the interior, anterior, and posterior necrotic zones (Dolle et al. (1989) Nature 342, 702-705; Mendelsohn et al. (1991) Development 113, 723-734). While null mutants of either RAR$\alpha$, RAR$\beta$ or RAR$\lambda$ exhibit no limb skeletal malformations (Ghyselinck et al. (1997) Int. J. Dev. Biol. 41, 425-44; Lohnes et al. (1993) Cell 73, 643-658; Lufkin et al. (1993) Proc. Natl. Acad. Sci. USA 90, 7225-7229; Luo et al. (1995) Mech. Dev. 53, 61-71), compound homozygous null alleles of RAR$\alpha$ and RAR$\lambda$ exhibit a range of severe limb abnormalities from reductions to duplications (Lohnes et al. (1994) Development 120, 2723-2748). Thus, these results demonstrate an important function for the RARs in skeletal development.

To further explore RAR function in limb development the present inventors have used an existing transgenic line of mice that overexpress a weak constitutively active RAR$\alpha$1 (caRAR$\alpha$) in the developing limb bud (Cash et al. (1997) J. Cell Biol. 136, 445-457). Transgenic animals present with a number of limb skeletal abnormalities as a result of transgene-mediated inhibition of cartilage formation. Transgene-expressing cells do not differentiate into chondroblasts, but instead remain as condensed mesenchyme. Conversely, an RAR$\alpha$ antagonist was demonstrated to stimulate cartilage formation in wild-type limb mesenchymal cultures. Addition of BMP-2 or -4 to in vitro cultures of transgenic mesenchyme dramatically stimulated condensation of transgene-expressing mesenchymal cells but failed to induce chondroblast differentiation. More importantly, addition of this antagonist was found to rescue chondrogenesis in noggin treated wild-type cultures. Taken together, the results demonstrate that loss of RAR activity is necessary, and supersedes the requirement of BMPs, for chondroblast differentiation during limb outgrowth.

Regulation of chondroblast differentiation is critical for the proper formation of the appendicular skeleton. Herein it is now demonstrated that RAR activity has a fundamental role in controlling the transition of prechondrogenic cells to chondroblasts, and that the loss of RAR activity stimulates cartilage formation. The importance of RARs in mediating chondroblast differentiation is further exemplified by the observations that addition of BMP-2 and -4 is not sufficient to rescue RAR$\alpha$ expressing prechondrogenic cells, while an RAR$\alpha$ specific antagonist is able to rescue cartilage formation in noggin-treated cultures. Therefore, BMPs and RARs function in a sequential manner to orchestrate chondroblast differentiation during limb bud outgrowth.

Function of RARs During Skeletal Development

Overexpression of a caRAR$\alpha$ in limb mesenchyme inhibits chondroblast differentiation and maintains the prechondrogenic cell phenotype. The phenotype of cells expressing the transgene is consistent with that of condensed mesenchymal cells and perichondrial cells. Both of these cell types are similar in that they are chondroprogenitors which have not yet undergone chondroblast differentiation. Condensed mesenchymal cells and perichondrial cells both have continued expression of N-cadherin, gli-1, and col-I but express col II only weakly, a pattern of expression that is seen in transgenic cultures. The normal expression pattern of RAR$\alpha$ in the developing limb is consistent with its absence being essential for the transition from a chondroprogenitor to a chondroblast. RAR$\alpha$ is expressed in the prechondrogenic condensations, the perichondrium, and in the interdigital region, but is down-regulated in newly formed cartilaginous elements. The importance of the loss of RAR$\alpha$ signal is further demonstrated by experiments in which the RAR$\alpha$ specific antagonist AGN194301 increased cartilage nodule formation in primary cultures by 60%. Hence, the proper regulation of RAR$\alpha$ activity is essential for normal cartilage development.

Surprisingly, RAR$\alpha$ null mutants display no overt skeletal malformations of the appendicular skeleton with the exception that a certain proportion (approx. 60% of animals surviving to 1-2 months of age) of RAR$\alpha$ null mutants have webbed digits (Lohnes et al. (1993) Development 120, 2723-2748; Lufkin et al. (1993) Proc. Natl. Acad. Sci. USA 90, 7225-7229. However, in micromass cultures, attenuation of RAR$\alpha$2 expression with an anti-sense oligonucleotide to RAR$\alpha$2 stimulated cartilage formation in vitro. This suggests that RAR$\alpha$ alone is not essential for the maintenance of the prechondrogenic cell fate, but one of the RARs may be able to substitute for this function, the most likely candidate being RAR$\gamma$. RAR$\gamma$ null mutants also have no obvious appendicular skeletal malformations. RAR$\alpha$/RAR$\gamma$ compound homozygous mutants, however, exhibit a number of skeletal defects including reductions, duplications, and to a lesser extent, ectopic cartilage formation within the interdigital region (Development 120, 2723-2748. Ectopic cartilages are also observed at a number of additional sites in these animals including the meninges, peritoneum, diaphragm, and semilunar cusps of the heart (Lohnes et al. (1994) Development 120, 2723-2748; Mendelsohn et al. (1994) Development 113, 723-734). In addition, the phalangeal joints of these animals are malformed. While RARα/β and RARβ/γ double knockouts exhibit some cartilaginous deficiencies, they do not present with any appendicular skeletal defects. More importantly, the skeletal defects in the RARα/γ double knockouts can be rescued, for the most part, by the single allele of RARα2.

Results from knockout studies combined with the in vivo expression patterns of RARs suggest that both RARα and RARγ are important in regulating chondroblast differentiation in the limb. RARβ knockouts exhibit no skeletal abnormalities, and RARβ mRNA is absent in precartilaginous condensations during limb ontogeny (Ghyselnick et al. (1997) Int. J. Dev. Biol. 41, 425-447). Thus, the combined activity of RARα and RARγ, but not RARβ is likely involved in regulating cartilage differentiation in the limb bud. In other areas of the developing embryo, chondrogenesis may also rely on the actions of specific combinations of RARs.

Sequential Action of BMPs and RARs in Skeletal Development

The BMPs have been shown to be important in many aspects of endochondral bone formation including the commitment and differentiation of mesenchymal cells to the chondrocytic lineage. During limb outgrowth bmp-2/-4 are expressed within the condensing mesenchyme, the perichondrium and the interdigital region (Jones et al. (1991) Development 111, 531-542; Lyons et al. (1990) Development 109, 833-844; Rosen et al. (1996) Ann. N.Y. Acad. Sci. 785, 59-69. Unfortunately, null mutants have not been informative in sorting out the function of BMPs-2/-4 in these regions (Winnier et al. (1995) Genes Dev. 9, 2105-2116; Zhang and Bradley (1996) Development 122, 2977-2986. Additional studies, utilizing dominant-negative or constitutively active BMP type II receptors in vitro and in vivo have demonstrated, however, that BMP signaling (most likely BMP-2 and 4) is a requisite step in cartilage formation (Zou et al. (1997) Genes Dev. 11, 2191-2203). These observations have been complemented by experiments in which BMPs were overexpressed in the developing chick limb. It has been demonstrated that the BMPs can stimulate cartilage formation (Duprez et al. (1996) Mech. Dev. 57, 145-157; Duprez et al. (1996) Dev. Biol. 174, 448-452) and modify skeletal element patterning in addition to stimulating apoptosis within the interdigital region (Macias et al. (1997) Development 124, 1109-1117; Yokouchi et al. (1996) Development 122, 3725-3734). Furthermore, loss or gain of function studies with noggin, an inhibitor of BMP-2 and -4 with lower affinity for BMP-7, has shown that BMP-2 and -4 are important in skeletal development and that regulation of BMP signaling is required for delineation of the various skeletal elements (Brunet et al. (1998) Science 280, 1455-1457; Capdevila and Johnson (1998) Dev Biol 197, 205-217). As described herein, exogenously added noggin inhibits cartilage formation in micromass cultures. BMP-2 has been shown to stimulate the commitment and differentiation of pluripotent mesenchymal cells to the chondrocytic lineage (Ahrens et al. (1993) DNA Cell Biol. 12, 871-880; Wang et al. (1993) Growth Factors 9, 57-71). Thus, BMPs, especially -2/-4, are important in early skeletal development, and appear to have properties consistent with a functional importance in commitment and differentiation of mesenchymal cells to chondrocytes.

Overexpression of a caRARα prevents prechondrogenic cell differentiation, even in the presence of BMP-2 or -4. Both BMP-2 and -4 enhance the expression of the prechondrogenic phenotype by stimulating the formation of numerous condensations as confirmed by magenta-gal staining and by in situ hybridization with probes for N-cadherin, gli-1, col-I and col-II. Nonetheless, neither BMP-2 nor BMP-4 was able to induce chondroblast differentiation of transgene-expressing cells. These results demonstrate that the regulation of RAR activity operates downstream of BMP-signaling in the chondroblast differentiation sequence. Additional evidence to suggest this comes from the observations that inhibition of cartilage formation by noggin can be circumvented by treatment of cultures with an RAR antagonist. During paraxial development, RARα, RARγ, are co-expressed in the condensing mesenchyme and in the perichondrium, which are both targets of BMP-2 and -4. Hence, these results suggest that during limb outgrowth BMP-2 and -4 are important in stimulating prechondrogenic cell condensation, whereas a loss of RARα activity is important in allowing the differentiation of these cells. In this manner, the BMP and RA-signaling pathways may function sequentially in the commitment and differentiation of mesenchymal cells, respectively, during limb outgrowth.

RAR Function in Chondroblast Differentiation: Conservation in Other Developmental Processes A similar hierarchy of BMP and RA signaling may be operating in other developmental processes. BMPs-2 and -4 and RARs are co-expressed in a number of different regions within the developing embryo. As mentioned previously, BMP-2 and -4 are co-expressed with RARα, β, and γ in the interdigital region. Application of BMPs to the interdigital region enhances interdigital apoptosis (Macias et al. (1997) Development 124, 1109-1117; Yokouchi et al. (1996) Development 122, 3725-3734), while overexpression of a dominant-negative BMPIIR inhibits interdigital apoptosis and webbed digits (Zou and Niswander (1996) Science 272, 738-741; Zou et al. (1997) Genes Dev. 11, 2191-2203). In addition, loss of RARα, or loss of β and γ together, leads to a cessation of interdigital apoptosis and webbed digits. When cultured prior to the initiation of apoptosis, explants of the interdigital region will form cartilage unless RA is present in which case they will undergo apoptosis (Lee et al. (1994) Dev. Dynam. 201, 297-309). Similarly, addition of RA to in vitro cultured limbs stimulates regression of the interdigital regions (Lussier et al. (1993) Int. J. Dev. Biol. 37, 555-564). Together, these observations suggest that the BMPs and RA-signaling pathways coordinate interdigital cell death, in addition to chondrogenesis.

During heart formation BMP-2 and -4 appear to be important in specifying ventricular cardiomyocytes whereas the RARs regulate the differentiation of this population of cells. Loss of RAR activity through inactivation of RXRα, RXRβ, RARα causes precocious differentiation of ventricular myocytes (Kastner et al. (1997) Development 124, 4749-4758). Hence, RARs are functioning in the heart to regulate progenitor cell differentiation as they do within the limb.

One of the functions of RARs in limb development is to regulate the differentiation of skeletal progenitor cells. In this manner, RAR activity may specify the size of progenitor cell populations, and/or influence cell fate decisions by modulating the competency of cells to respond to inductive signals, such as BMPs. The status of cellular RAR activity, therefore, appears to be an important determinant in the spatiotemporal regulation of cell differentiation in the developing limb, heart and spinal cord.

RAR Antagonists

With the demonstration that RAR antagonist compounds can act as potent stimulators of chondrogenesis and associated skeletal development, various therapeutic in vivo and in vitro uses of such antagonists are now made possible especially those uses involving abnormal chondrogenesis and related skeletal development.

The RAR antagonist AGN 194301, shown in Table 1, has been demonstrated to stimulate cartilage formation and promote chondroblast differentiation. AGN 194301 (2-Fluoro-4-[(1-(8-bromo-2,2-dimethyl-4-(4-methylphenyl)-2-H-chromen-6-yl)-methanoyl)-amino]-benzoic acid) is a potent antagonist of RAR$\alpha$, with a high affinity for that receptor. It has a lower affinity for RAR$\beta$ and RAR$\gamma$, but does also act as an antagonist of these receptors.

In accordance with one embodiment of the invention, chondrogenesis-stimulating RAR antagonists comprise antagonist compounds which are highly effective against RAR$\alpha$ and also antagonise RAR$\beta$ and RAR$\gamma$. Thus, the present invention encompasses RAR antagonists in general and any agent which demonstrates RAR antagonist activity. Those of ordinary skill in the art are able to screen candidate compounds to identify compounds having such an RAR antagonist profile by methods available in the scientific literature, for example as described in Teng et al. (1997) J. Med. Chem. 40, 2445-2451.

In accordance with one embodiment of the invention, chondrogenesis-stimulating RAR antagonists comprise mono- or di-fluoro substituted methylchromenes such as AGN 194301. The RAR antagonist compounds of the invention may be synthesized by conventional chemical synthetic methods. For example, AGN 194301 may be synthesised as described in Teng et al. (supra). In some cases, suitable RAR antagonists may be purchased.

One skilled in the art would readily understand that several different types of RAR antagonists other than those described specifically herein are suitable for use in the present invention. Other suitable RAR antagonists are taught for example in WO 9933821, WO 9924415, U.S. Pat. No. 5,877,207 and JP 10114757. Such antagonist agents include but are not limited to AGN 193109, AGN 190121, AGN 194574, AGN 193174, AGN 193639, AGN 193676, AGN 193644, SRI 11335, Ro 41-5253, Ro 40-6055, CD 2366, BMS 185411, BMS 189453, CD-2665, CD 2019, CD 2781, CD 2665, CD 271. Other suitable RAR antagonists for use in the present invention include those disclosed in Kaneko et al. (1991) Med. Chem. Res. 1, 220-225; Apfel et al. (1992) Proc. Natl. Acad. Sci. U.S.A. 89, 7129-7133; Eyrolles et al. (1994) J. Med. Chem. 37, 1508-1517; Yoshimura et al. (1995) J. Med. Chem. 38, 3163-3173; Eckharat and Schmitt (1994) Toxicol. Lett. 70, 299-308; and Teng et al. (1997) J. Med. Chem. 40, 2445-2451.

The chondrogenesis-stimulating RAR antagonists of the invention are useful for the treatment and management of skeletal problems or abnormalities resulting from disease or trauma in vertebrates, including humans and other mammals, including horses. They may be used in several therapeutic applications where increased chondrogenesis is desired and also for stimulation of skeletal development.

Therapeutic applications of these antagonists include the stimulation of new cartilage formation and accelerate associated bone repair through endochondral ossification.

A pharmaceutical composition comprising at least one chondrogenesis-stimulating RAR antagonist may be applied locally to a fracture site, for example by means of a biodegradable sponge, gel, coating or paste. A suitable gel for use would be a collagen type gel such as collagen I.

The antagonists of the present invention may also be used for the treatment of orthopedic or dental implants to enhance or accelerate osseous integration. A pharmaceutical composition comprising at least one chondrogenesis-stimulating RAR antagonist may be directly applied locally to the site of desired osseous integration or alternatively as a coating on implants.

The RAR antagonists may also be used for promoting in vivo integration of implantable prosthetic devices. In general, the RAR antagonist compositions of the invention may be applied to synthetic bone grafts for implantation whereby the antagonist composition stimulates cartilage formation and indirectly bone formation. The compositions thus have numerous applications in the orthopedic industry. In particular, there are applications in the fields of trauma repair, spinal fusion, reconstructive surgery, maxillo-facial surgery and dental surgery. The ability of the RAR antagonist compositions to stimulate local natural bone growth provides stability and rapid integration, while the body's normal cell-based bone remodeling process slowly resorbs and replaces a selected implant with natural bone. Implants suitable for in vivo use are generally known to those skilled in the art.

The RAR antagonists of the invention may be used for cartilage and skeletal reconstruction. In such an application, the antagonists can be used for ex vivo tissue engineering of cartilage or skeletal tissue for implantation in a vertebrate. Cells can be treated with a RAR antagonist during osteochondral autograft or allograft transplantations (Minas et al. (1997) Orthopedics 20, 525-538). In autograft transplantations, chondrogenic cells or cells with chondrogenic potential are removed from a patient (e.g. from a rib) and used to fill a cartilaginous lesion. An alternative method involves expanding these cells in vitro, then implanting them into a cartilaginous lesion. A pharmaceutical composition comprising at least one chondrogenesis-stimulating RAR antagonist would be used to treat the cells in in vitro culture prior to engraftment and/or after engraftment through intra-articular injection. The use of the RAR compositions of the invention may eliminate the pain and costs associated with the bone harvest procedure required in autograft transplants. Furthermore, the RAR compositions can be made synthetically thus reducing the possibility of transmission of infection and disease, as well as diminishing the likelihood of immunological rejection by the patient.

The antagonist compositions of the present invention may also be used for the treatment of arthritis, either osteoarthritis or other types of arthritis including rheumatoid arthritis. To reverse or slow degenerative joint disease characterized by cartilage degeneration, a pharmaceutical composition comprising at least one chondrogenesis-stimulating RAR antagonist would be applied locally through intra-articular injection or in combination with a viscosupplement. The composition could be provided in either a fast-release or slow-release formulation. Such compositions have use in patients with degenerative hip or knee joints, for example.

In general, the RAR antagonists may be used to stimulate in vitro chondrogenesis from mesenchymal precursor cells and in vitro formation of chondrocytes. Such cell culture materials and methods are known to those skilled in the art and are also described herein in the examples. Cells and tissues treated with a selected RAR antagonist in vitro can be used therapeutically in vivo or alternatively for in vitro cellular assay systems.

The pharmaceutical compositions of the invention may be used in combination with other chondrogenic stimulators, e.g. bone morphogenetic proteins (BMPs) especially BMP-2 and BMP-4, osteogenic proteins (OPs) such as OP-1 and/or cytokines to enhance and/or maintain the effects of the compositions. Both BMPs and OPs are proteins belonging to the TGF-β superfamily which represent proteins involved in growth and differentiation as well as tissue morphogenesis and repair. It is also understood that the RAR antagonist compositions of the invention may additionally comprise other chondroinductive agents or factors, defined as any natural or synthetic organic or inorganic chemical or biochemical compound, or mixture of compounds which stimulate chondrogenesis. It is further understood that the RAR antagonist compositions of the invention may also comprise other growth factors known to have a stimulatory effect on cartilage growth and formation.

The RAR antagonist compositions described herein appear to have a more dramatic effect on chondrocyte function than the BMPs and show longer-lived effects. The RAR antagonists are also more cost effective to manufacture than BMPs.

Those of ordinary skill in the art are familiar with various methods of formulating pharmaceutical compositions for local administration in diseases such as arthritis. For example, Adams et al. (1995) Osteoarthritis & Cartilage 3, 213-225, describes viscosupplementation in osteoarthritis; Wozney and Rosen (1998) Clin. Ortho. Rel. Res. 346, 26-37, describes delivery methods used for BMPs to effect bone repair and formation. These formulation methods may be employed to prepare the RAR compositions of the invention.

For therapeutic applications in accordance with the present invention the RAR antagonists are incorporated into pharmaceutical compositions formulated for oral or parenteral administration, the latter route including intravenous and subcutaneous administration. Parenteral administration may be by continuous infusion over a selected period of time. As such, the compositions may be provided as tablets, pills, capsules, solutions, suspensions, creams, gels, and the like.

An RAR antagonist may be orally administered with an inert diluent or with an assimilable edible carrier, or it may be enclosed in hard or soft shell gelatin capsules, compressed into tablets or incorporated directly with the food of the diet. For oral therapeutic administration, the RAR antagonist may be incorporated with excipient and used in the form in ingestible tablets, buccal tablets, troches, capsules, elixirs, suspensions, syrups, wafers, and the like.

In one embodiment of the present invention, a pharmaceutical composition for administration to subjects in a biologically compatible form suitable for administration in vivo for treating abnormal chrondrogenesis and associated skeletal development comprises a safe and effective amount of a selected RAR antagonist alone, or in combination with other agents and/or pharmaceutically acceptable carriers. The composition may be administered to any living organism including humans and animals. By "safe and effective amount" as used herein is meant providing sufficient potency in order to decrease, prevent, ameliorate or treat a chondrogenesis or skeletal disorder affecting a subject while avoiding serious side effects. A safe and effective amount will vary depending on the age of the subject, the physical condition of the subject being treated, the severity of the disorder, the duration of treatment and the nature of any concurrent therapy. Dosage regima may be adjusted to provide the optimum therapeutic response. For example, several divided doses may be administered daily or the dose may be proportionally reduced as indicated by the exigencies of the therapeutic situation. The compositions are preferably in the form of a unit dose and will usually be administered as a dose regimen that depends on the particular tissue treatment.

The compositions described herein can be prepared by known methods for the preparation of pharmaceutically acceptable compositions which can be administered to subjects, such that an effective quantity of the active substance is combined in a mixture with a pharmaceutically acceptable carrier. By pharmaceutically acceptable carrier as used herein is meant one or more compatible conventional solid or liquid delivery systems as are well known in the art. Some examples of pharmaceutically acceptable carriers are sugars, starches, cellulose and its derivatives, powdered tragacanth, malt, gelatin, collagen, talc, stearic acids, magnesium stearate, calcium sulfate, vegetable oils, polyols, agar, alginic acids, pyrogen-free water, isotonic saline, phosphate buffer, and other suitable non-toxic substances and medicinal agents used in pharmaceutical formulations. Other excipients such as wetting agents and lubricants, tableting agents, stabilizers, anti-oxidants and preservatives are also contemplated. Suitable carriers are further described for example in Remington's Pharmaceutical Sciences (Remington's Pharmaceutical Sciences, Mack Publishing Company, Easton, Pa., USA 1985). On this basis the compositions include, albeit not exclusively, solutions of the substance in association with one or more pharmaceutically acceptable vehicles or diluents, and contained in buffered solutions with a suitable pH and iso-osmotic with the physiological fluids.

The RAR antagonist compositions of the invention can be provided as a liquid for local administration at a desired tissue site such as by injection. Alternatively, the compositions of the invention can be provided encapsulated for administration to a desired tissue site. In one embodiment, the RAR antagonist composition may comprise at least one RAR antagonist which may be provided as a solution or emulsion contained within phospholipid vesicles called liposomes. The liposomes may be unilamellar or multilamellar and are formed of constituents selected from phosphatidylcholine, dipalmitoylphosphatidylcholine, cholesterol, phosphatidylethanolamine, phosphatidylserine, demyristoylphosphatidylcholine and combinations thereof. The multilamellar liposomes comprise multilamellar vesicles of similar composition to unilamellar vesicles, but are prepared so as to result in a plurality of compartments in which the silver component in solution or emulsion is entrapped. Additionally, other adjuvants and modifiers may be included in the liposomal formulation such as polyethyleneglycol, or other materials.

It is understood by those skilled in the art that any number of liposome bilayer compositions can be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101.

The liposomes containing the RAR antagonist may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules which preferentially target the liposome to specific organs or cell types include for example antibodies which target the liposomes to cells bearing specific antigens. Techniques for coupling such molecules are well known to those skilled in the art (see for example U.S. Pat. No. 4,762,915 the disclosure of which is incorporated herein by reference). Alternatively, or in conjunction, one skilled in the art would understand that any number of lipids bearing a positive or negative net charge may be used to alter the surface charge or surface charge density of the liposome membrane.

The liposomes can also incorporate thermal sensitive or pH sensitive lipids as a component of the lipid bilayer to provide controlled degradation of the lipid vesicle membrane.

For systemic application by intravenous delivery, it may be beneficial to encapsulate the RAR antagonist within sterically-stabilized liposomes which exhibit prolonged circulation time in blood. The sterically stabilized liposomes are produced containing polyethylene glycol as an essential component of their surface and the method of making such liposomes is known to those skilled in the art.

The size of the liposomes can be selected based on the intended target and route of administration. Liposomes of between about 10 nm to 300 nm may be suitable. Furthermore, the composition of the present invention may include liposomes of different sizes.

While the composition of the present invention may be encapsulated for administration by liposomes, it is understood by those skilled in the art that other types of encapsulants may also be used to encapsulate the RAR antagonist. Microspheres including but not limited to those composed of ion-exchange resins, crystalline ceramics, biocompatible glass, latex and dispersed particles are suitable for use in the present invention. Similarly, nanospheres and other lipid, polymer or protein materials can also be used.

The RAR antagonist compositions of the present invention may comprise a RAR antagonist dispersed in an implantable biocompatible carrier that functions as a suitable delivery or support system for the antagonist. Suitable examples of biocompatible sustained release carriers include semi-permeable polymer matrices in the form of shaped implantable articles such as polylactides, copolymers of L-glutamic acid, ethyl-L-glutamate, poly(2-hydroyethyl-methacrylate) or ethylene vinyl acetate. Such matrices can be fabricated to have the RAR antagonist incorporated therein and be of a selected pore size to permit chondroprogenitor cells and skeletal progenitor cells to migrate within. The selected carrier material may also comprise a biodegradable, synthetic or synthetic-organic matrix such as hydroxyapatite, collagen, tricalcium phosphate or various copolymers of glycolid, lactic and butyric acid.

The RAR antagonist composition of the present invention may also be used with demineralized allogenic bone and demineralized xenogenic bone optionally treated with fibril modifying agents. Furthermore, the composition may be provided with a mechanical or suitable physical device, influence or force such that it functions to promote chondrogenesis and skeletal development either in vitro or in vivo.

In summary, RAR antagonists have important clinical therapeutic uses for treatment of cartilage and associated bone development defects. The RAR antagonists can be used to provide such treatment both in vitro and in vivo to treat a variety of conditions as a result of trauma, genetic disease or degenerative disease negatively affecting cartilage and associated bone development and maintenance.

EXAMPLES

The examples are described for the purposes of illustration and are not intended to limit the scope of the invention.

Methods of chemistry, protein and peptide biochemistry, cell biology, molecular biology and immunology referred to but not explicitly described in this disclosure and examples are reported in the scientific literature and are well known to those skilled in the art.

Methods

Preparation of Micromass Cultures

Micromass cultures were prepared from murine E11.25 to E11.75 fore and hind limb buds as previously described with the following modifications (Cash et al. (1997) J. Cell Biol. 136, 445-457). After proteolytic digestion cells were filtered through a Cell Sieve (40 µM, Falcon) to obtain a single cell suspension. Culture media (40% Dulbecco's modified Eagle's medium, 60% F12 was supplemented with fetal bovine serum to 10%, Gibco-BRL) was changed daily. BMP-2 or -4 (Genetics Institutes), AGN 194301 (Allergan Pharmaceuticals) and/or purified Xenopus noggin protein was added to culture media at a concentration of 10 ng/ml, 1 µM and 10 ng/ml, respectively. Addition/removal experiments included either adding or removing supplemented media on the indicated culture day, 24 hours after culture initiation was considered day 1. To detect transgene-expressing cells, cultures were fixed stained as previously described, with magenta-gal (BioSynth International Inc.) being substituted for X-gal. This was followed by alcian blue staining for cartilage-specific glycosaminoglycans. Alcian blue staining of magenta-gal stained cultures turned the red precipitate to a purple color, this is a result of incubating magenta-gal stained cells at pH 1. This double-staining technique enables transgene-expressing cells to be localized with respect to alcian blue stained cartilage nodules.

Synthesis of Riboprobes

Riboprobes were synthesized in the presence of UTP-digoxigenin with the appropriate RNA polymerase and linearized template DNA according to the manufacturers directions (Boehringer Mannheim Corp., Indianapolis, Ind.). Riboprobe complementary to collagen type II gene, was generated from Bam H1 linearized pBluescript containing 1.1 kb of the collagen type II gene containing the C-propeptide and transcribed in vitro with T7 RNA polymerase. Gli-1 riboprobe was transcribed from Not 1 linearized pBluescript containing a 1.6 kb fragment representing most of the zinc finger domain of gli-1. A 553 bp fragment of murine collagen type I (Phillips et al. (1992) Genomics 13, 1345-1346) was subcloned into pKS II (Stratagene), this was linearized with Xho1 and transcribed with T7 RNA polymerase. A Hind III (position 605)-BamH1 (position 1252) fragment from the mouse N-cadherin cDNA was subcloned into pKSII. This construct was linearized with Bam H1 and riboprobe synthesized with T7 RNA polymerase. For controls, sense riboprobes were synthesized from the aforementioned plasmids.

Whole-Mount in situ Hybridization of Micromass Cultures

In situ hybridizations were carried out on micromass cultures using a technique described previously (Cash et al. (1997) J. Cell Biol. 136, 445-457), with minor modifications. After permeabilization using 10 µg/ml proteinase-K in phosphate buffered saline (PBS) supplemented with 0.05% Triton X-100, cells were post-fixed in 4% paraformaldehyde and 2% glutaraldehyde in PBS and hybridizations were carried out at 60° C. instead of 55° C.

Transient Transfection Analysis

The ability of AGN194301 to inhibit all-trans RA induction of an RARE containing luciferase construct was performed in P19 embryonal carcinoma cells as previously described with some modification (Underhill et al. (1994) Mol. Endo. 8, 274-285). P19 cells were seeded at a density of 1.5×10⁴ cells/well in 6 well plates. Cells were transfected using the calcium phosphate precipitation method with each well receiving 3.9 μg DNA (1.25 μg pW1RAREtk-lucif, 0.33 μg pW1ActRARα/β/γ, 0.67 μg pW1Actβ-galactosidase and 1.65 μg pGEM9zf(−)). Following transfection cells were washed and fresh media was added that contained $1×10^{-7}$ M all-trans RA and various amounts of AGN194301. Twenty-four hours later cell extracts were prepared, and luciferase and β-galactosidase activity measured. Luciferase activity was normalized with β-galactosidase activity to control for differences in transfection efficiency.

Northern Blot Analysis

Total RNA was isolated dissected and pooled limb buds from wild-type and transgenic embryos at various gestational stages with TriPure Isolation Reagent (Boehringer Mannheim). RNA samples were separated by electrophoresis of 15 μg aliquots in a 1% agarose-formaldehyde gel. RNA was then transferred to a Hybond-N nylon membrane (Amersham Life Science) and cross-linked by UV irradiation. Blots were pre-hybridized in Church's Buffer (7% SDS, 0.5 M NaPi pH 7.2, 1 mM EDTA, 1% BSA) at 65° C. for at least 30 min. Radio-labeled DNA probes were synthesized by random priming using standard methods with the appropriate cDNA insert fragments. Hybridizations were carried out overnight at 60° C. Following hybridization blots were washed with wash buffer (250 mM NaPi, 10% SDS) three times for 15 min. at 65° C., and exposed to BioMax X-ray film at −80° C. for 1-4 days:

Example 1

Transgene-expressing Cells Do Not Contribute to Cartilage Nodule Formation

To further demonstrate the role of the RARs, specifically RARα, during cartilage formation, we used a previously described transgenic mouse model (Cash et al. (1997) J. Cell Biol. 136, 445-457). Overexpression of a weak constitutively active RARα during limb development leads to various congenital malformations of the limb that are reminiscent of those observed in RA teratogenicity. During chondroblast differentiation, RARα expression is down-regulated. The continued expression of RARα inhibits chondroblast differentiation leading to a cessation of cartilage formation and to skeletal deficiencies as observed in the transgenic mice. Limb mesenchyme from embryonic age (E) 11.5 transgenic embryos was used to set up micromass cultures to examine the cell fate of transgene-expressing cells during in vitro chondrogenesis. Shown in FIG. 1 is a time-course of cartilage nodule formation (day-2, day-4 and day-6) in wild-type (FIGS. 1A, B, and C) and transgenic fore limb cultures (FIG. 1E, 1F, 1G) and hind limb cultures (FIG. 1H, day-4 shown). Consistent with previous observations there are many fewer alcian blue-stained nodules in the transgenic derived cultures than in the wild-type cultures. Using a combination of magenta-gal and alcian blue staining, we clearly show that transgene-expressing cells are, for the most part, excluded from the cartilage nodules (FIG. 1D) but appear to form condensations. Transgene-expressing cells fail to differentiate into chondroblasts in contrast to both non-transgene-expressing cells within the same cultures, and cells within wild-type cultures.

Example 2

Transgene-expressing Cells Have a Prechondrogenic Phenotype

Figure 2A:
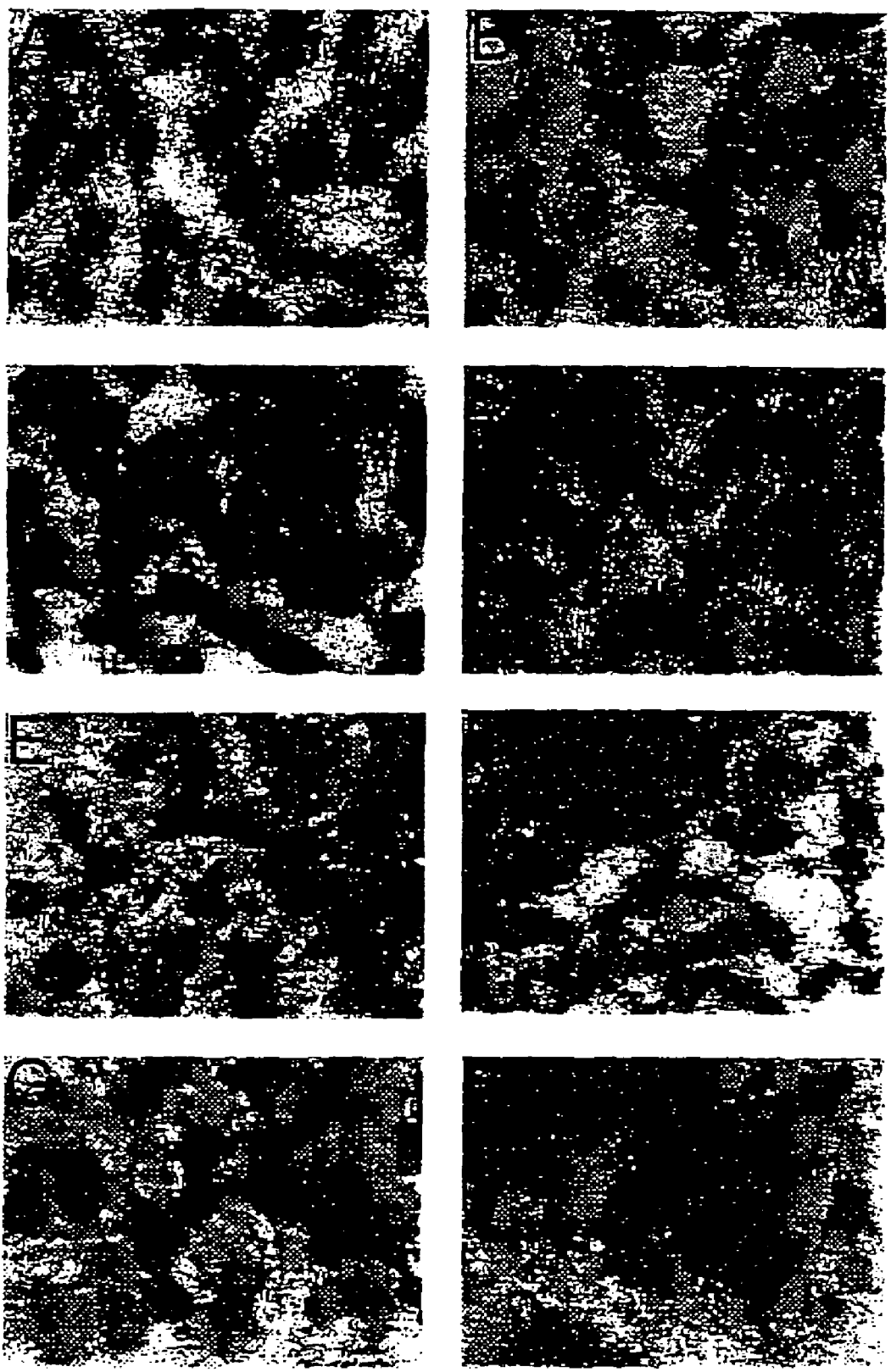
FIG. 2A shows photomicrographs of transgene-expressing cells. Panels (A-H) show whole mount in situ hybridization of wild-type and transgenic cultures carried out using probes characteristic of specific stages of chondrogenesis. Panel (A) shows Col II expression is very abundant in wild-type cultures. Panel (B) shows Col II expression in transgenic cultures is much weaker and has a more widespread distribution. Panels (C, E, G) show wild-type cultures, N-cad, gli-1, and col I are all abundantly expressed in perinodular regions but are only weakly expressed in the core of the nodules. Panels (D, F, H) show that in transgenic cultures, N-cad, gli-1 and col-I are expressed throughout the cultures with no apparent downregulation as seen in the center of the nodules of wild-type cultures. Bar: (A-H) 0.4 mm.
Figure 2B:
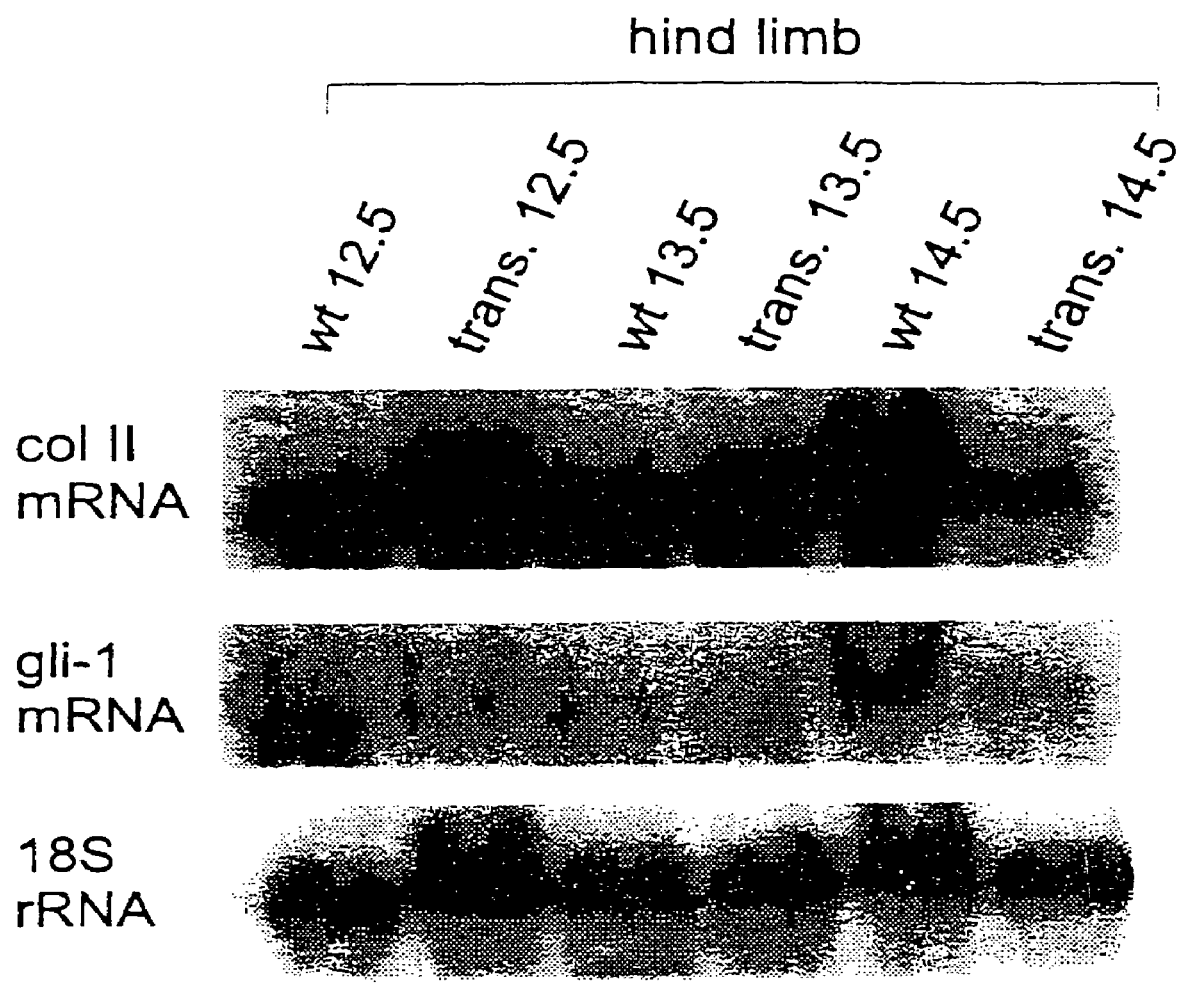
FIG. 2B shows the results of northern blot analysis using total hind limb bud RNA indicating that col II is downregulated in transgenic hind limbs at E 14.5, and gli-1 is downregulated in transgenic hind limbs at E 12.5.

Cartilage formation involves two well described steps: 1) condensation of mesenchymal cells; 2) differentiation of condensed mesenchyme to matrix-producing chondrocytes (Hall and Miyake (1992) Anat. Embryol. 186, 107-124). These two stages can be distinguished based on histological staining, however, using molecular markers is generally a more reliable method for determining the phenotype of cells at either stage. Previous studies have shown that condensed prechondrogenic cells express col II weakly and express N-cad, col I and gli-1 abundantly (Hall and Miyake (1995) Int. J. Dev. Biol. 39, 881-893; Marigo et al. (1996) Dev. Biol. 180, 273-283; Oberlender and Tuan (1994) Cell Adhes Commun 2, 521-537. Upon differentiation of these cells, col II expression becomes much stronger, whereas expression of N-cad, col I, and gli-1 are down-regulated. To further characterize the phenotype of the transgene-expressing cells, whole mount in situ hybridization was carried out to examine the expression patterns of col II, N-cad, col I and gli-1 in transgenic and wild-type cultures. In wild-type cultures, col II expression was very strong and localized primarily to the core of the cartilage nodules with weaker expression in regions surrounding the nodules (FIG. 2A). Expression of N-cad, col I and gli-1 in wild-type cultures was restricted to perinodular regions in condensed mesenchyme and was weakly expressed in the centre of the nodules (FIGS. 2C, E and G). The expression patterns of these genes in the wild-type cultures is consistent with their expression in vivo. In transgenic cultures, however, their expression patterns would indicate that while condensations are present the condensed cells have not yet differentiated. There was no downregulation of N-cad, col I or gli-1, instead they were expressed throughout the condensations (FIGS. 2D, F and H), whereas col II was only weakly expressed (FIG. 2B), resembling a pattern one would expect to see in condensations but not in cartilage nodules. These observations demonstrate that the transgene-expressing cells condense but do not undergo chondroblast differentiation.

Comparison of the distribution of col II expression in transgenic and wild-type cultures suggests that the transgenic cultures form a similar number of condensations as observed in wild-type cultures (FIG. 2A, B). Furthermore, the col II stained regions in transgenic and wild-type cultures are similar in size indicating that transgene-mediated inhibition of chondroblast differentiation was not a consequence of insufficient numbers of prechondrogenic cells (Hall and Miyake (1992) Anat. Embryol. 186, 107-124). Moreover, during the culture period the transgene-expressing cell aggregates continue to expand in size and staining intensity (FIGS. 1E, 1F and 1G). Northern blot analysis has confirmed differential expression of col II and gli-1 between the hind limbs of wild-type and transgenic mice. By E 14.5, col II is downregulated in transgenic hind limbs (FIG. 2I), whereas gli-1 is downregulated in transgenic hind limb at E 12.5 (FIG. 2I). The in situ hybridization results combined with results from Northern blot analysis demonstrate that the phenotype displayed by transgene-expressing cells is consistent with condensed prechondrogenic cells.

Example 3

Transgene-expressing Cells are Refractile to BMP-stimulated Chondroblast Differentiation To further investigate the mechanism of transgene-mediated inhibition of chondroblast differentiation, the expression of genes known to be important in chondrogenesis, namely the BMPs was examined. Based on their expression in limb development and their well defined chondrogenic stimulatory properties, the analysis was focused on bmps-2 and -4. Hence, one plausible explanation for the transgenic phenotype was either the reduced expression of bmps or overexpression of noggin which encodes an inhibitor of BMP signaling. Northern analysis using mRNA from hind limbs of transgenic and wild-type animals at E 11.5, 12.5, and E 14.5 demonstrated that neither bmp2 nor noggin is differentially expressed in transgenic animals in comparison to wild-type animals (data not shown). The defect in transgenic limb mesenchyme therefore is not likely a result of changes in expression of either of these two transcripts. However, these results do not preclude the possibility that transgene-expressing mesenchymal cells are unresponsive to BMPs.

Figure 3A:
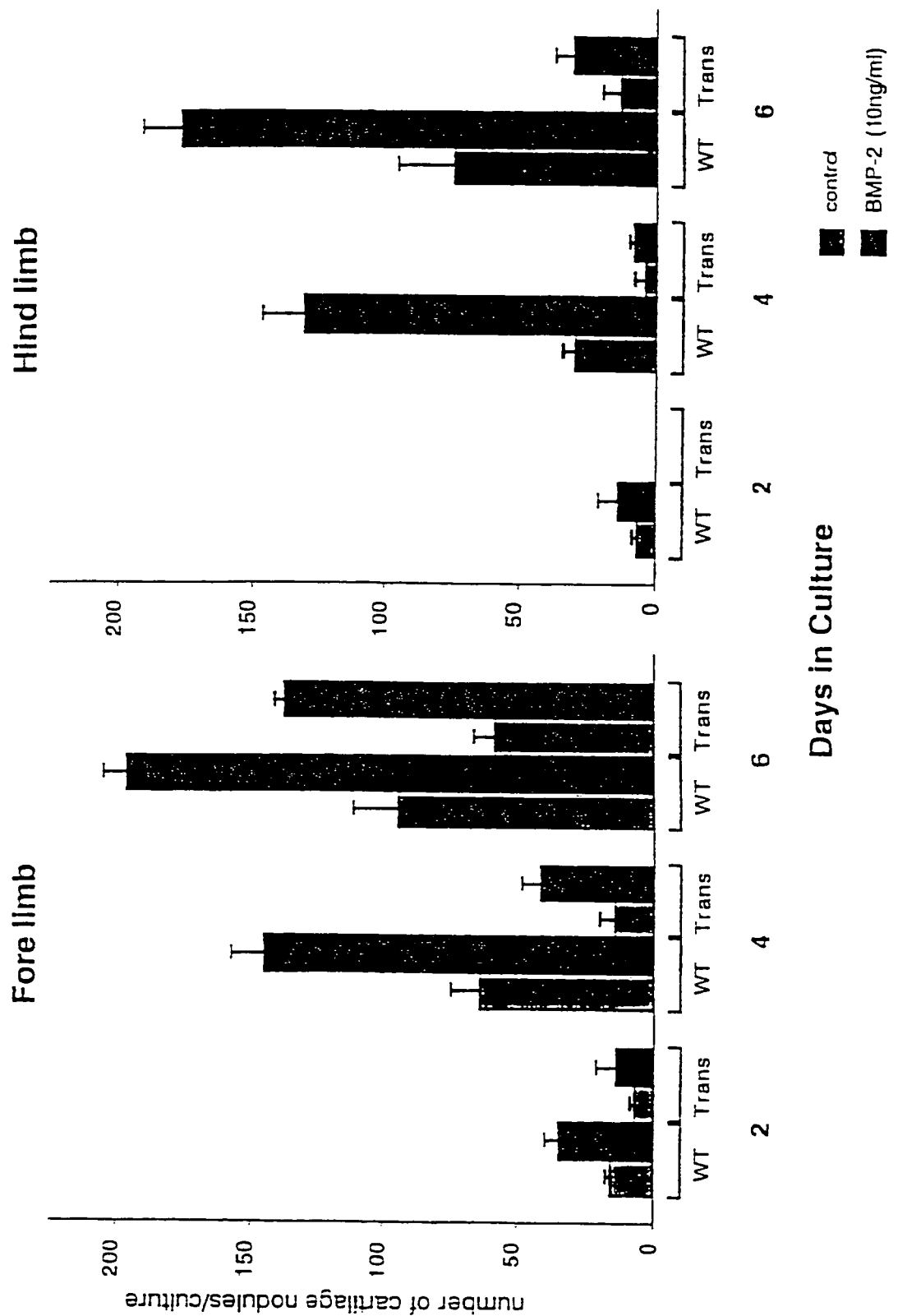
FIG. 3 shows transgene-expressing cells respond differently to BMP-2. Panel (A) shows quantitative analysis of nodule formation in vitro. There are fewer cartilage nodules in the fore and hind limb cultures of untreated transgenic cultures compared to those in untreated wild-type cultures. BMP-2 treatment increases the number of nodules in both wild-type and transgenic cultures, however, the increase seen in wild-type cultures is more dramatic. Panels (B-D) show wild-type cultures treated with BMP-2 stained with alcian blue at days 2, 4 and 6. In response to BMP-2, there is a noticeable increase in nodule number and in nodule size, with cartilage nodules located at the periphery of the cultures becoming the largest. Panels (F-H) show transgenic cultures treated with BMP-2 and stained with magenta-gal followed by alcian blue at days 2, 4 and 6. In response to BMP-2 there is an increase in nodule number and in nodule size. There are also many more condensations of transgene-expressing cells. Panel (E) shows higher magnification of day 4 wild-type cultures treated with BMP-2. Panel (I) shows higher magnification of day 4 transgenic cultures treated with BMP-2. BMP-2 stimulates condensation of transgene-expressing cells, but they remain excluded from cartilage nodules. Bar: (A-C, E-G) 1.0 mm (D, H) 0.4 mm.
Figures 3B, 3C, 3D, 3E, 3F, 3G, 3H, 3I:
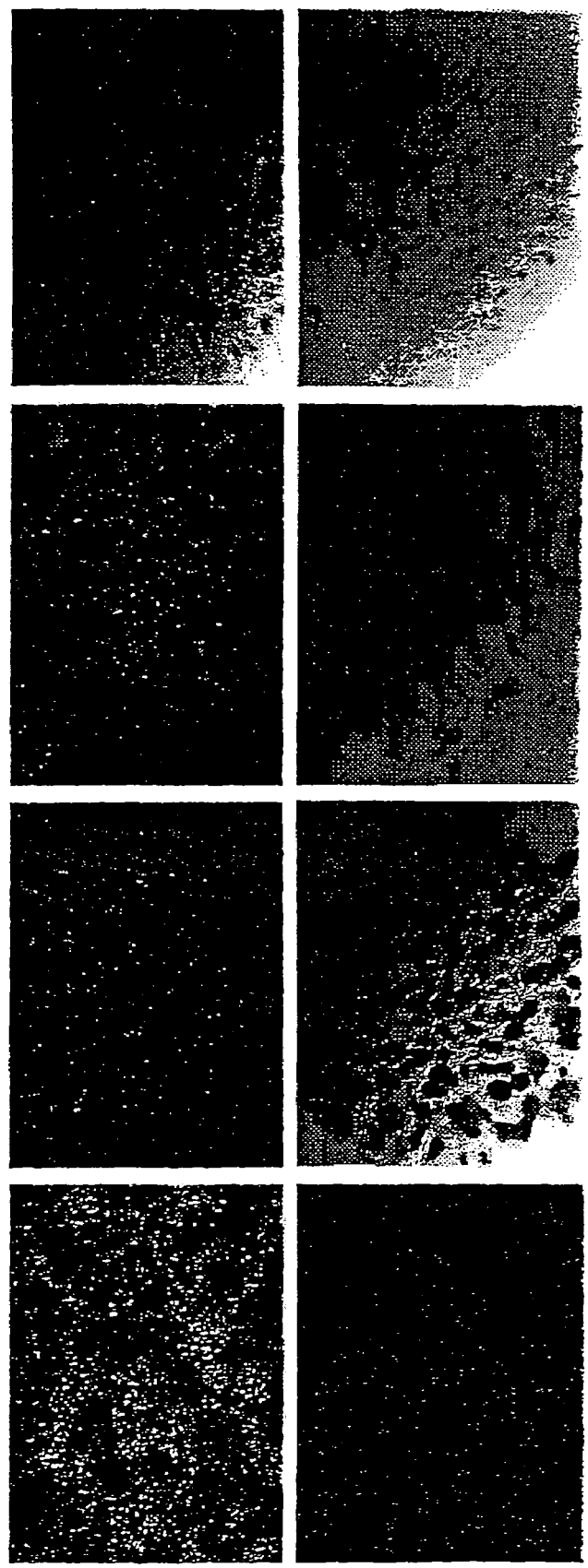
Figure 4:
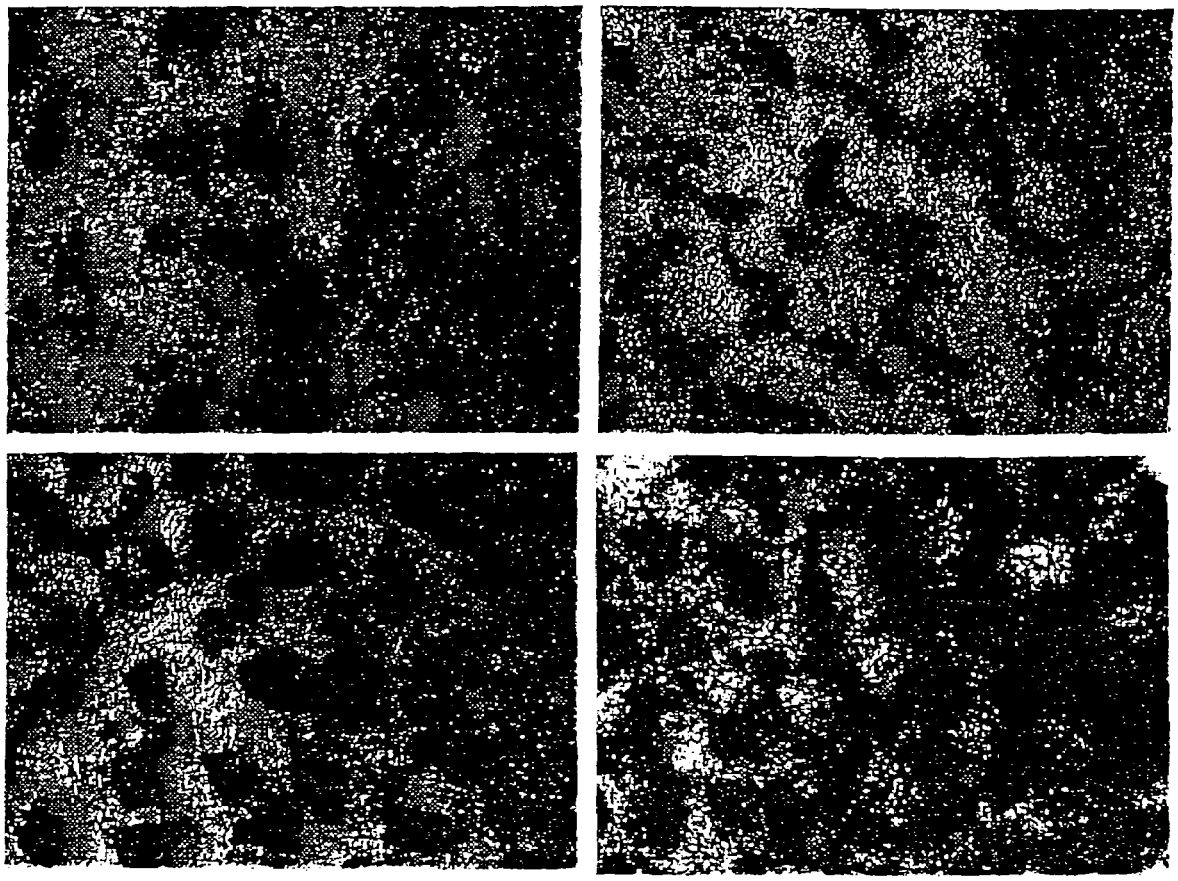
FIG. 4 shows Col II expression is altered in transgenic cultures. Panels (A, B) show Col II expression in wild-type and transgenic cultures respectively. In wild-type cultures, col II is abundantly expressed within cartilage nodules and is much weaker in transgenic cultures with a less distinct expression pattern. Panel (C) shows that in response to BMP-2 the number of cartilage nodules in wild-type cultures that express col II abundantly increases. Panel (D) shows that in transgenic cultures treated with BMP-2 there are a few nodules with abundant col II expression and several condensations with weaker expression. Bar: (A-D) 0.4 mm.

To evaluate whether transgene-expressing cells are able to respond to BMPs, transgenic and wild-type micromass cultures were treated with 10 ng/ml BMP-2 and -4. It was demonstrated that addition of BMP-2 (FIG. 3A) and -4 dramatically increases the number of cartilage nodules in wild-type and transgenic cultures. BMP-2 treatment for six days increased the number of cartilage nodules by ~125% and ~115% in wild-type and transgenic fore limb cultures, respectively (FIG. 3A-I). Hence, addition of BMP-2 or -4 appears to rescue the chondrogenic defect present in transgenic cultures. To confirm this, BMP-2 treated cultures were stained with magenta-gal followed by alcian blue (FIGS. 3F, G and H). As observed in non-treated transgenic cultures, few if any transgene-expressing cells were found to be present within the alcian blue stained cartilage nodules (FIG. 3I). Addition of BMP-2, however, stimulated condensation of transgene-expressing cells (FIG. 3F-I). This was confirmed by in situ hybridization, BMP-2 addition stimulated the formation of col II expressing nodules and weak col II condensations in wild-type and transgenic cultures, respectively (FIG. 4). Condensations were observed as early as 2 days in culture and were still evident after 6 days in culture. Thus, although BMP-2 or -4 induces transgene-expressing cells to form precartilaginous condensations they are not sufficient to overcome transgene-mediated inhibition of prechondrogenic cell differentiation.

Example 4

Loss of Retinoic Acid Receptor Activity Stimulates Chondrogenesis

Figures 5A, 5B, 5C, 5D, 5E, 5F, 5G, 5H, 5I, 5J, 5K, 5L:
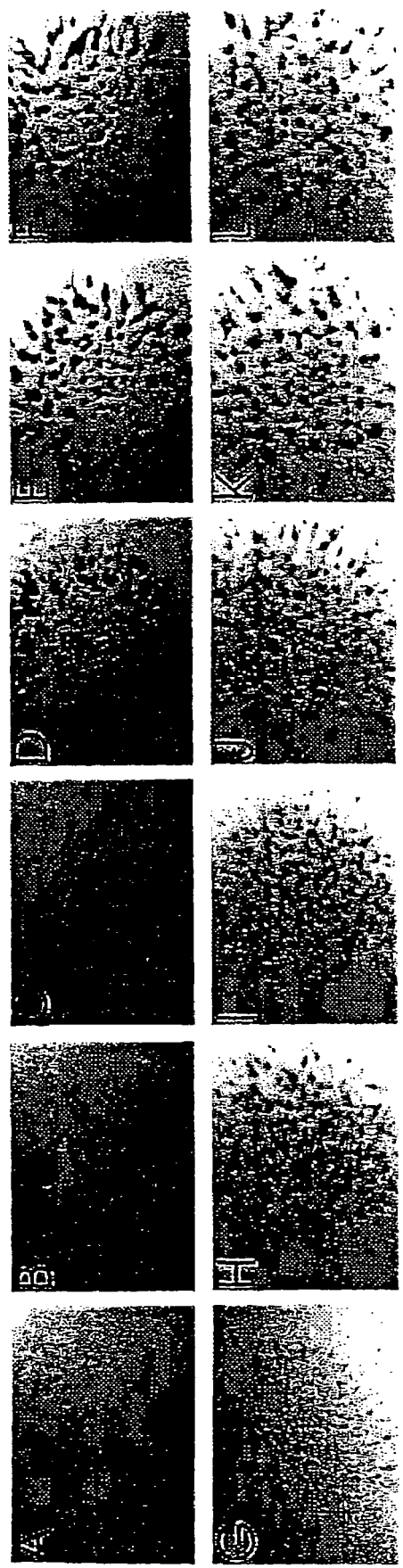
FIG. 5 shows BMP-2 and AGN194301 exhibit different chondrogenic stimulatory properties. Panel (A) shows untreated wild-type cultures stained with alcian blue on day 6. Panels (B, C) show wild-type cultures treated with BMP-2 for the first two days and three days of culture, respectively, and stained with alcian blue on day 6. These cultures resemble untreated cultures. Panel (D) shows wild-type cultures treated continuously with BMP-2 and stained with alcian blue on day 6. Panels (E, F) show wild-type cultures were treated after two or three days respectively and stained with alcian blue on day 6. These cultures resemble cultures that were treated continuously with BMP-2. Panel (G) shows untreated wild-type cultures stained with alcian blue on day 8. Panels (H, I) show wild-type cultures treated with AGN194301 for the first two days and three days of culture, respectively, and stained with alcian blue on day 8. These cultures resemble cultures treated continuously with AGN194301 in that there are several smaller nodules. Panel (J) shows wild-type cultures were treated continuously with AGN194301 and stained with alcian blue on day 8. Panels (K, L) show wild-type cultures treated after two or three days respectively and stained with alcian blue at day 8. The size and number of cartilage nodules is less compared to cultures treated continuously. Bar: (A-L) 1.0 mm. Panel (M) shows quantification of cartilage nodule formation in response to BMP-2 and AGN194301. In response to BMP-2, or AGN194301 alone, there is a dramatic increase in the number of nodules that form. When BMP-2 and AGN194301 are added together, the number of nodules formed is greater than when each is added alone.
Figure 5M:
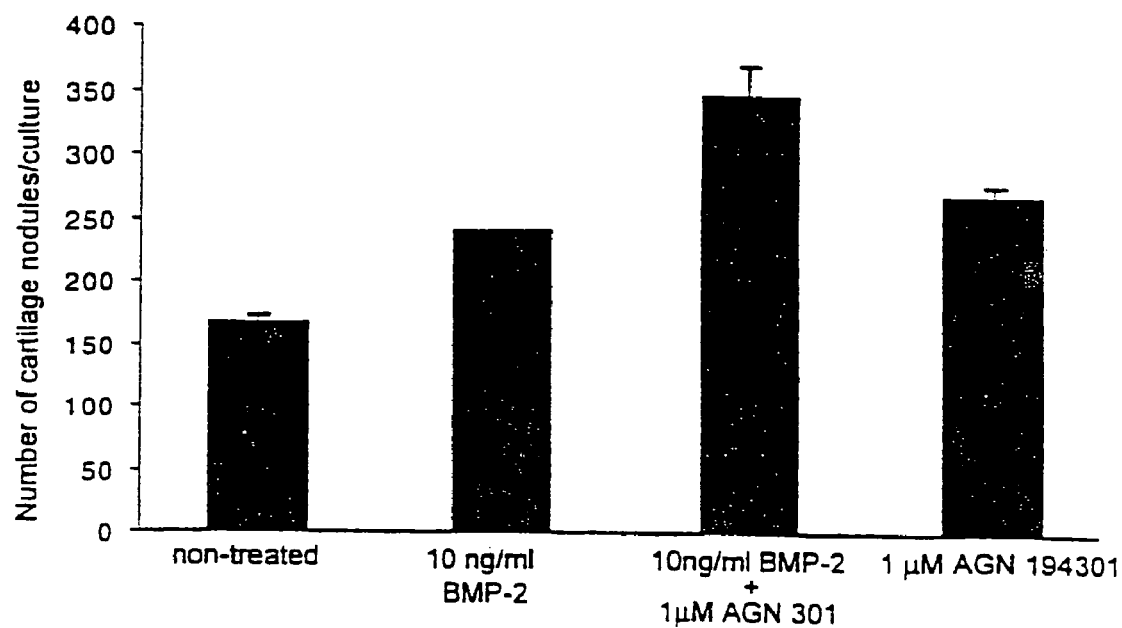

It has presently been demonstrated that the continued expression of RARα inhibits the transition of prechondrogenic cells to chondroblasts. It was then demonstrated that the abrogation of RARα activity stimulated chondroblast differentiation and/or cartilage formation. RAR activity as used herein refers to the level of RA-induced transcriptional activity of the RARs. Micromass cultures were treated with the RARα-specific antagonist AGN194301 to examine whether inhibition of RARα activity stimulated cartilage formation. Addition of 1 μM AGN194301 to wild-type micromass cultures lead to a dramatic increase in nodule number with no apparent increase in nodule size as compared to untreated control cultures (FIG. 5G, J, M). After 8 days in culture there were 60% more nodules in antagonist treated cultures than in untreated cultures (FIG. 5M). Similar to the inhibition of cartilage nodule formation observed in response to all-trans RA treatment of micromass cultures, addition of the RARα-specific agonist AGN 193836 at 1 μM, decreased the number of cartilage nodules that formed by 35% with the nodules staining only weakly with alcian blue. To confirm that the concentrations utilized in these experiments inhibited RARα activity specifically, the level of RARα, RARβ and RARγ mediated RARE activation was measured with 100 nM all-trans RA in the presence of various concentrations of antagonist. At 1 μM of AGN194301, RARα signaling was inhibited to ~0.3% of controls, while RARβ and RARγ were inhibited to ~18% and ~26% of controls, respectively. Hence, most of the chondrogenic stimulatory properties of the antagonist appear to be mediated through inhibition of RARα, however, it cannot be entirely discounted that diminution of RARβ or RARγ signaling may have contributed to these results. Nonetheless, loss of RAR activity stimulates cartilage formation while increased RAR activity inhibits cartilage formation.

Example 5

The RAR Antagonist and BMP-2 Have Different Chondrogenic Stimulatory Properties The loss of RAR activity and addition of BMP-2 both stimulate cartilage formation. In transgenic cultures, BMP-2 stimulated condensation but not differentiation of transgene-expressing cells, whereas a loss of RARα activity induced cartilage formation. These results suggest that the two factors: a) BMP-2 availability and b) RARα activity are important at different stages during chondrogenesis. To further delineate the role of BMP-2 and RARα in cartilage formation, we have used an approach that involves incubation of micromass cultures with AGN194301 or BMP-2 for different periods of time during culturing. To accomplish this BMP-2 or AGN194301 were added to cultures for the first 2 or 3 days then removed, or were added after 2 or 3 days of culturing. As has been shown previously (Roark and Greer (1994) Dev. Dynam. 200, 103-116), addition of BMP-2 at later culture periods yielded results that are comparable to experiments in which BMP-2 is added continuously from the start of culture (FIG. 5D-F). Conversely, addition of BMP-2 for the first 2 to 3 days of culture caused an increase in nodule number but this increase was not as dramatic as that observed upon adding BMP-2 later (i.e., after 2 or 3 days). The average size of the nodules was also noticeably increased in cultures that were either continuously exposed to BMP-2 or treated after 2 or 3 days of culture (FIG. 5B-F). These large nodules radiate towards the outside of the culture and are, in part, a consequence of the recruitment of proliferating uncommitted cells present in the periphery of the culture into the nodules. Similar observations have been made with BMP-2 addition in vivo as Duprez et al. (Duprez et al. (1996) Mech. Dev. 57, 145-157) showed that expansion of skeletal elements in the presence of BMP-2 or -4 was at the expense of other cell populations in the developing chick limb bud. Hence, the consequences of BMP-2 addition are much more pronounced in cultures treated at later stages of culture and likely reflect the ability of BMP-2 to stimulate commitment of mesenchymal cells to the chondrocytic lineage with subsequent recruitment into nodules.

In contrast to BMP-2 and -4, AGN194301 had its most pronounced stimulatory effect on nodule formation when it was present early in the culture period. When 1 μM AGN194301 was added to cultures for only the first 2 or 3 days, then removed, more cartilage nodules were formed compared to untreated cultures (FIG. 5G-I) or to cultures exposed for longer periods of time but untreated for the first 2 or 3 days (FIG. 5K, L). Interestingly, the increase in nodule number caused by early treatment of the antagonist was maintained for 4 or more days after its removal and was comparable to the increase in nodule number observed with continuous treatment (FIG. 5H-J). AGN194301, therefore, caused an increase in nodule formation, however the nodules were much smaller compared to cultures receiving antagonist at later culture times. When BMP-2 and AGN194301 were added together to micromass cultures at a concentration of 10 ng/ml and 1 µM, respectively, there was a ~100% increase in nodule number compared to untreated controls (FIG. 5M). BMP-2 addition alone to cultures initiated from the same limb buds caused a ~45% increase, whereas AGN194301 treatment caused an increase of ~60% (FIG. 5M). Together, these results demonstrate that the loss of RAR activity and the presence of a BMP signal are two events that act at different stages of the chondrogenic sequence as they exhibit markedly different chondrogenic stimulatory properties.

Example 6

Figure 6:
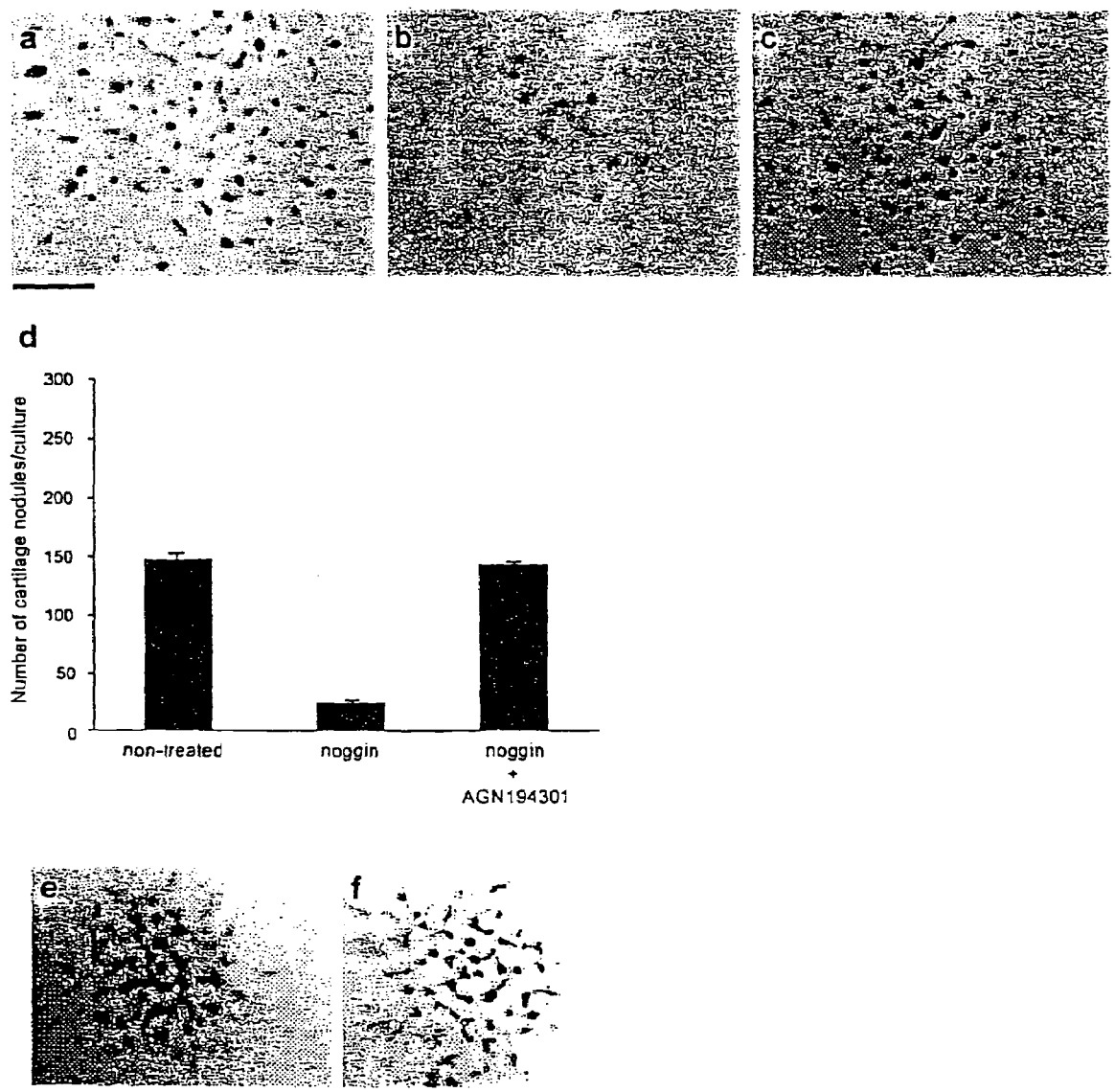
FIG. 6 shows the rescue of cartilage formation in Noggin-treated cultures by addition of AGN194301. Panel (a) shows wild-type cultures stained with alcian blue on day 6. Panel (b) shows wild-type cultures treated with Noggin (10 ng/ml) and stained with alcian blue on day 6. In comparison to control cultures, only a few weakly stained nodules are evident and these are present within the center of the culture where cell density is highest. Panel (c) shows wild-type cultures treated with 10 ng/ml Noggin and 1 µM AGN194301. When Noggin and AGN 194301 are added together, there is no apparent decrease in nodule formation in comparison to untreated cultures. Similar to that observed in control cultures, nodules are distributed throughout the culture. Panel (d) shows the quantification of cartilage nodule formation in response to Noggin and AGN194301. Treatment of Noggin alone dramatically reduced the number of cartilage nodules to ~10% of that of control cultures. Addition of AGN194301 to Noggin-treated cultures rescues cartilage formation and leads to an increase in cartilage nodule formation comparable to that of control cultures. Panels (e, f) show the analysis of col IIa and col II expression in Noggin-treated cultures, respectively, revealing a comparable number of col 2a expressing aggregates and col II expressing nodules. The bar represents 1 mm.

Cartilage Formation is Rescued in Noggin-treated Cultures by Addition of an RARα Antagonist To further address the requirement for BMPs in chondrogenesis, wild-type limb mesenchyme cultures were treated with Noggin, a secreted inhibitor of BMP-2, and -4. Addition of 10 ng/ml Noggin to wild-type cultures dramatically reduced cartilage nodule formation by ~84% in comparison to untreated controls (FIGS. 6a, b and d). In an attempt to define the chondrogenic stage affected by Noggin, cultures treated with Noggin were examined for the expression of col II and col IIA an alternatively spliced form of col II expressed in prechondrogenic cells (Sandell et al. 1991; Sandell et al. 1994). In limb bud derived cultures col IIA is expressed in the condensing mesenchyme surrounding cartilaginous nodules and in precartilaginous condensations (FIG. 6e, f). If Noggin delays or inhibits chondroblast differentiation but does not affect condensation, then the decrease in col II expressing nodules should be accounted for by col IIA expressing condensations. In contrast, however, comparison of expression of these two genes by in situ hybridization in Noggin-treated cultures indicates there are no additional condensations present (FIG. 6e, f). Hence, Noggin appears to interfere with formation of precartilaginous condensations.

Earlier experiments in which addition of BMP-2 was unable to rescue cartilage in transgene-expressing cultures coupled with the accelerated appearance of col II expressing cells in antagonist-treated cultures demonstrated that loss of RAR activity alone is sufficient to initiate the chondrogenic differentiation program. To further demonstrate this, Noggin-treated cultures were exposed to the RAR antagonist. The addition of 1 µM AGN194301 to Noggin-treated cultures, stimulated cartilage nodule formation such that these cultures resembled untreated cultures (FIGS. 6a, c and d). In contrast, addition of 10 or 20 nM all-trans RA further diminished nodule formation in Noggin-treated cultures (data not shown). These results indicate that suppression of RAR-mediated signaling not only stimulates expression of the chondrogenic phenotype, but can do so independently of a BMP signal.

TABLE 1

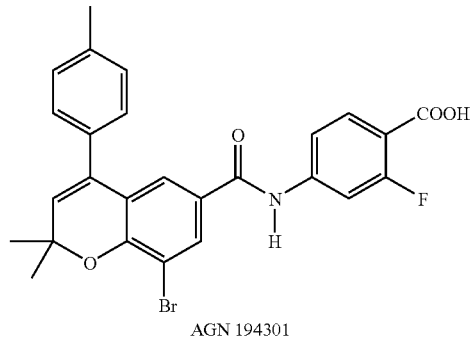

AGN 194301

2-Fluoro-4-[(1-(8-bromo-2,2-dimethyl-4-(4-methylphenyl)-
2-H-chromen-6-yl)-methanoyl)-amino]-benzoic acid

The invention claimed is:

1. A method for treating degenerative joint disease characterized by cartilage degeneration comprising:
   delivering a therapeutically effective amount of an RAR antagonist to the site of disease to stimulate chondrogenesis at said site of disease, wherein said RAR antagonist is provided within a composition comprising a pharmaceutically acceptable carrier and a chondrogenic stimulator.

2. The method according to claim 1, wherein said chondrogenic stimulator is a protein selected from the group consisting of a bone morphogenetic protein (BMP), an osteogenic protein (OP), and combinations thereof.

3. The method according to claim 2, wherein said osteogenic protein is OP-1.

4. The method according to claim 1, wherein said composition is provided as a solution, suspension, gel, matrix, cream, film, paste, capsule, pill or tablet, or is encapsulated within liposomes.

5. The method according to claim 1, wherein said composition is for intra-articular injection.

6. The method according to claim 1, wherein said composition is provided within a biodegradable implantable matrix.

7. The method according to claim 1, wherein said composition is for the treatment of arthritis, abnormal cartilage formation and/or cartilage defects.

8. The method according to claim 1, wherein said RAR antagonist antagonizes one or more of RARα, RARβ and RARγ.

9. A method for treating degenerative joint disease characterized by cartilage degeneration comprising:
   delivering a therapeutically effective amount of an RAR antagonist to the site of disease to stimulate chondrogenesis at said site of disease, wherein said method comprises implanting a device comprising:
   (a) an implantable biocompatible carrier; and
   (b) the RAR antagonist dispersed within or on said carrier, wherein said carrier comprises demineralized bone, protein-extracted bone, particulate bone, allogenic bone, xenogenic bone or combinations thereof.

10. The method according to claim 9, wherein said device comprises a biodegradable sponge.

11. The method according to claim 9, wherein said device is a prosthetic for repairing an orthopaedic defect, injury or anomaly in a vertebrate.

12. The method according to claim 11, wherein said device has a surface region implantable adjacent or within a target tissue and said RAR antagonist is disposed on said surface region in an amount sufficient to promote enhanced chondrogenesis and associated bone tissue growth into said surface.

13. The method according to of claim 9, wherein said RAR antagonist is provided within a composition further comprising a pharmaceutically acceptable carrier and a chondrogenic stimulator.

14. The method according to claim 13, wherein said chondrogenic stimulator is a protein selected from the group consisting of a bone morphogenetic protein (BMP), an osteogenic protein (OP), and combinations thereof.

15. The method according to claim 2, wherein said BMP is selected from the group consisting of BMP-2, BMP-4 and BMP-5.

* * * * *